US011013421B2

(12) United States Patent
Narasimhan

(10) Patent No.: US 11,013,421 B2
(45) Date of Patent: May 25, 2021

(54) BLOOD PRESSURE ESTIMATION USING FINGER-WEARABLE SENSOR ARRAY

(71) Applicant: Verily Life Sciences LLC, Mountain View, CA (US)

(72) Inventor: Ravi Narasimhan, Sunnyvale, CA (US)

(73) Assignee: VERILY LIFE SCIENCES LLC, Mountain View, CA (US)

( * ) Notice: Subject to any disclaimer, the term of this patent is extended or adjusted under 35 U.S.C. 154(b) by 439 days.

(21) Appl. No.: 15/809,895

(22) Filed: Nov. 10, 2017

(65) Prior Publication Data
US 2019/0104953 A1 Apr. 11, 2019

Related U.S. Application Data

(60) Provisional application No. 62/570,503, filed on Oct. 10, 2017.

(51) Int. Cl.
*A61B 5/022* (2006.01)
*A61B 5/00* (2006.01)
*A61B 5/021* (2006.01)

(52) U.S. Cl.
CPC ........ *A61B 5/02241* (2013.01); *A61B 5/0004* (2013.01); *A61B 5/02108* (2013.01);
(Continued)

(58) Field of Classification Search
CPC .............. A61B 5/02241; A61B 5/0002; A61B 5/02108; A61B 5/021; A61B 5/0205;
(Continued)

(56) References Cited

U.S. PATENT DOCUMENTS 5,533,511 A * 7/1996 Kaspari .............. A61B 5/02007
600/485
5,762,610 A * 6/1998 Narimatsu ......... A61B 5/02116
600/500
(Continued)

FOREIGN PATENT DOCUMENTS

| DE | 10 2015 103 261 | 1/2016 |
| EP | 0818176 A1 | 1/1998 |
| WO | 2016/040256 A1 | 3/2016 |

OTHER PUBLICATIONS

International Search Report and Written Opinion from the International Searching Authority dated Nov. 21, 2018, for International Application No. PCT/US2018/050956, filed Sep. 13, 2018, 13 pages.
(Continued)

*Primary Examiner* — Patrick Fernandes
(74) *Attorney, Agent, or Firm* — Christensen O'Connor Johnson Kindness PLLC

(57) ABSTRACT

A finger-wearable blood pressure monitor device includes a cuff, a tactile sensor array, and control circuitry. The tactile sensor array is disposed on or adjacent to an inward facing surface of the cuff. The tactile sensor array includes a plurality of sensors. The control circuitry is coupled to the tactile sensor array and includes logic that when executed by the control circuitry causes the finger-wearable blood pressure monitoring device to perform operations. The operations include monitoring, over a first time period, a pressure applied to each of the plurality of sensors by a digital artery of a finger. The operations also include generating a plurality of tactile waveforms in response to monitoring the pressure. Each of the plurality of tactile waveforms corresponds to the pressure applied to a respective one of the plurality of sensors over the first time period. The operations further
(Continued)

include estimating blood pressure based, at least in part, on the plurality of tactile waveforms.

27 Claims, 16 Drawing Sheets

(52) U.S. Cl.
CPC ...... *A61B 5/02125* (2013.01); *A61B 5/02225* (2013.01); *A61B 5/6826* (2013.01); *A61B 5/6843* (2013.01); *A61B 5/725* (2013.01); *A61B 5/7221* (2013.01); *A61B 5/7235* (2013.01); *A61B 5/7246* (2013.01); *A61B 5/7264* (2013.01); *A61B 5/7278* (2013.01); *A61B 2560/0214* (2013.01); *A61B 2562/0247* (2013.01); *A61B 2562/043* (2013.01); *A61B 2562/046* (2013.01)

(58) Field of Classification Search
CPC . A61B 5/02125; A61B 5/6826; A61B 5/6843; A61B 5/7221; A61B 5/7264; A61B 5/0004; A61B 5/02225; A61B 5/725; A61B 5/7246; A61B 5/7278; A61B 2560/0214; A61B 2562/0247; A61B 2562/043
See application file for complete search history.

(56) References Cited

U.S. PATENT DOCUMENTS

| | | | |
|---|---|---|---|
| 7,674,231 | B2 | 3/2010 | McCombie et al. |
| 8,814,800 | B2 | 8/2014 | Fortin et al. |
| 9,345,424 | B2 | 5/2016 | Wang et al. |
| 2002/0177781 | A1* | 11/2002 | Amano ............ A61B 5/021 600/485 |
| 2007/0167844 | A1* | 7/2007 | Asada ............ A61B 5/022 600/485 |
| 2010/0286538 | A1 | 11/2010 | Kim et al. |
| 2013/0144176 | A1 | 6/2013 | Lec |
| 2014/0323891 | A1 | 10/2014 | Sterling et al. |
| 2015/0272452 | A1 | 10/2015 | Mullin et al. |
| 2015/0327784 | A1 | 11/2015 | Lading et al. |
| 2016/0113589 | A1 | 4/2016 | Yoon |
| 2016/0198955 | A1 | 7/2016 | Fortin |
| 2017/0055854 | A1 | 3/2017 | Chouciar et al. |
| 2017/0238878 | A1* | 8/2017 | Lading ............ A61B 5/7221 |
| 2017/0258336 | A1* | 9/2017 | Furness, III ........ A61B 5/026 |

OTHER PUBLICATIONS

Calhoon, Jennifer, "Tactile Sensors Support Next Generation Medical Devices", Design World Online, Jan. 18, 2017, 3 pages.
Gizdulich, Paolo et al., "Models of Brachial to Finger Pulse Wave Distortion and Pressure Decrement", Cardiovascular Research vol. 33, 1997, pp. 698-705.
Chen, Chen-Huan et al., "Estimation of Central Aortic Pressure Waveform by Mathematical Transformation of Radial Tonometry Pressure", Circulation vol. 95, 1997, pp. 1827-1836.
International Search Report and Written Opinion from the International Searching Authority dated Apr. 11, 2018, for International Application No. PCT/US2018/012404, filed Jan. 4, 2018, 14 pages.
Babbs, C.F., "Oscillometric Measurement of Systolic and Diastolic Blood Pressures Validated in a Physiologic Mathematical Model," BioMedical Engineering OnLine 11:56, Dec. 2012, pp. 1-22.
Baker, P.D., et al., "Theoretical Analysis of Non-Invasive Oscillometric Maximum Amplitude Algorithm for Estimating Mean Blood Pressure," Medical and Biological Engineering and Computing 35(3):271-278, May 1997.
Chen, S., et al., "Assessment of Algorithms for Oscillometric Blood Pressure Measurement," Proceedings of the International Instrumentation and Measurement Technology Conference (I2MTC 2009), Singapore, May 5-7, 2009, 5 pages.
"Continuous Noninvasive Arterial Pressure," Wikipedia, The Free Encyclopedia <https://en.wikipedia.org/wiki/Continuous_noninvasive_arterial_pressure?oldid+675060442>, 6 pages.
Da Fonseca, L.J.S., et al., "Radial Applanation Tonometry as an Adjuvant Tool in the Noninvasive Arterial Stiffness and Blood Pressure Assessment," World Journal of Cardiovascular Diseases 4(5):225-235, May 2014.
Digiglio, P., et al., "Microflotronic Arterial Tonometry for Continuous Wearable Non-Invasive Hemodynamic Monitoring," Annals of Biomedical Engineering 42(11):2278-2288, Nov. 2014.
Doshi, H., et al., "Does 'Hidden Undercuffing' Occur Among Obese Patients? Effect of Arm Sizes and Other Predictors of the Difference Between Wrist and Upper Arm Blood Pressures," Journal of Clinical Hypertension 12(2):82-88, Feb. 2010.
Drzewiecki, G., et al., "Theory of the Oscillometric Maximum and the Systolic and Diastolic Detection Ratios," Annals of Biomedical Engineering 22(1):88-96, Jan. 1994.
Drzewiecki, G.M., et al., "Arterial Tonometry: Review and Analysis," Journal of Biomechanics 16(2):141-152, 1983.
Forouzanfar, M., et al., "Ratio-Independent Blood Pressure Estimation by Modeling the Oscillometric Waveform Envelope," IEEE Transactions on Instrumentation and Measurement 63(10):2501-2503, Oct. 2014.
"High Blood Pressure," Statistical Fact Sheet, 2014 Update, American Heart Association, 2 pages.
"High Blood Pressure Facts," Centers for Disease Control and Prevention (CDC), Nov. 30, 2016 <https://www.cdc.gov/bloodpressure/facts.htm%5C>, 5 pages.
"Integrated Capacitive Pressure Sensors," Fraunhofer IMS, 2-page brochure.
"Invasive Blood Pressure," © Memscap, Mar. 23, 2018 <http://www.memscap.com/applications-and-market-segments/medical-and-biomedical/invasive-blood-pressure>, 1 page.
Jílek, J., and M. Štork, "The Effect of Wrist Cuff Width on Oscillometric Blood Pressure Waveforms," Electroscope, vol. 2008, No. III, 2008, 4 pages.
Jones, R.D.M., et al., "The Finapres 2300e Finger Cuff: The Influence of Cuff Application on the Accuracy of Blood Pressure Measurement," Anaesthesia 48(7):611-615, Jul. 1993.
Kountz, D.S., et al., "MD Mouse, a New Finger Blood Pressure Monitor, Consistently Underestimates Blood Pressure Compared to a Standard Automatic Syphygnomanometer," Abstract P-54, Journal of the American Society of Hypertension 9(4S):e35-e488, 2015.
Lan, H., et al., "Effect of Tissue Mechanical Properties on Cuff-Based Blood Pressure Measurements," Medical Engineering and Physics 33(10):1287-1292, Dec. 2011.
Lee, J., and K.C. Nam, "Tonometric Vascular Function Assessment," Chap. 30, in Barros de Mello (ed.), "Biomedical Engineering," Intech Europe, Rijeka, Croatia, 2009, pp. 549-566.
Lee, J., et al., "Comparison Between Dynamic Contour Tonometry and Goldmann Applanation Tonometry," Korean Journal of Ophthalmology 23(1):27-31, Mar. 2009.
Lee, J.Y., et al., "Blood Pressure Measurement Using Finger Cuff," Proceedings of the 27th Annual Conference of IEEE Engineering in Medicine and Biology, Shanghai, Sep. 1-4, 2005, 3 pages.
Liu, J., et al., "Patient-Specific Oscillometric Blood Pressure Measurement," IEEE Transactions on Biomedical Engineering 63(6):1220-1228, Jun. 2016.
Lyew, M.A., and J.W. Jamieson, "Blood Pressure Measurement Using Oscillometric Finger Cuffs in Children and Young Adults," Anaesthesia 49(10):895-899, Oct. 1994.
McEniery, C.M., et al., "Central Blood Pressure: Current Evidence and Clinical Importance," European Heart Journal 35(26):1719-1725, Jul. 2014.
Miyashita, H., "Clinical Assessment of Central Blood Pressure," Current Hypertension Reviews 8(2):80-90, May 2012.
Ogedegbe, G., and T. Pickering, "Principles and Techniques of Blood Pressure Measurement," Cardiology Clinic 28(4):571-586, Nov. 2010. (Author Manuscript provided, PMCID:PMC3639494, available in PMC Apr. 30, 2013, 26 pages.).

(56) References Cited

OTHER PUBLICATIONS

Pickering, T.G., et al., "Recommendations for Blood Pressure Measurement in Humans and Experimental Animals, Part 1: Blood Pressure Measurement in Humans," Circulation 111(5):697-716, Feb. 2005.

Raamat, R., et al., "Mathematical Modelling of Non-Invasive Oscillometric Finger Mean Blood Pressure Measurement by Maximum Oscillation Criterion," Medical & Biological Engineering & Computing 37(6):784-788, Nov. 1999.

Rosatella, G., et al., "Non Invasive Procedure to Evaluate the Viscoelastic Behavior of the Brachial Artery by Oscillometric Repeated Measurements," Proceedings of the 25th Annual International Conference of the IEEE EMBS, Cancun, Mexico, Sep. 17-21, 2003, pp. 3302-3305.

Schattenkerk, D.W.E., et al., "Nexfin Noninvasive Continuous Blood Pressure Validated Against Riva-Rocci/Korotkoff," American Journal of Hypertension 22(4):378-383, Apr. 2009.

Valentinuzzi, M.E., and A.J. Kohen, "Laplace's Law: What It Is About, Where It Comes From, and How It Is Often Applied in Physiology," IEEE Pulse 2(4):74-84, Jul.-Aug. 2011.

Van Bortel, L.M., et al., "Non-Invasive Assessment of Local Arterial Pulse Pressure: Comparison of Applanation Tonometry and Echo-Tracking," Journal of Hypertension 19(6):1037-1044, Jun. 2001.

Communication Pursuant to Article 94(3) EPC dated Apr. 13, 2021, for corresponding European Patent Application No. 187892823, 5 pages.

\* cited by examiner

BLOOD PRESSURE ESTIMATION USING FINGER-WEARABLE SENSOR ARRAY

CROSS REFERENCE TO RELATED APPLICATIONS

This application claims the benefit of U.S. Provisional Application No. 62/570,503, filed on Oct. 10, 2017, the contents of which are incorporated herein by reference.

TECHNICAL FIELD

This disclosure relates generally to blood pressure monitoring, and in particular but not exclusively, relates to estimating blood pressure with a blood pressure monitor at a digital artery.

BACKGROUND INFORMATION

High blood pressure is a health concern for a large percentage of the population, but regular monitoring is not common-place. Blood pressure monitors are conventionally found in physician's offices, hospitals, pharmacies, and occasionally in homes. However, those who suffer from high blood pressure may only occasionally monitor their blood pressure during a visit to the physician's office visit or while waiting for a prescription at the pharmacy. Additional monitoring of blood pressure is requested by many physicians, but patients may not follow through due to difficulty in obtaining readings, expense of portable units, or the associated discomfort while using the blood pressure monitor. The associated discomfort is typically due to the squeezing of the arm or wrist, for example. As such, it may be desirable to have portable, easy to use, and more comfortable painful blood pressure monitoring devices.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
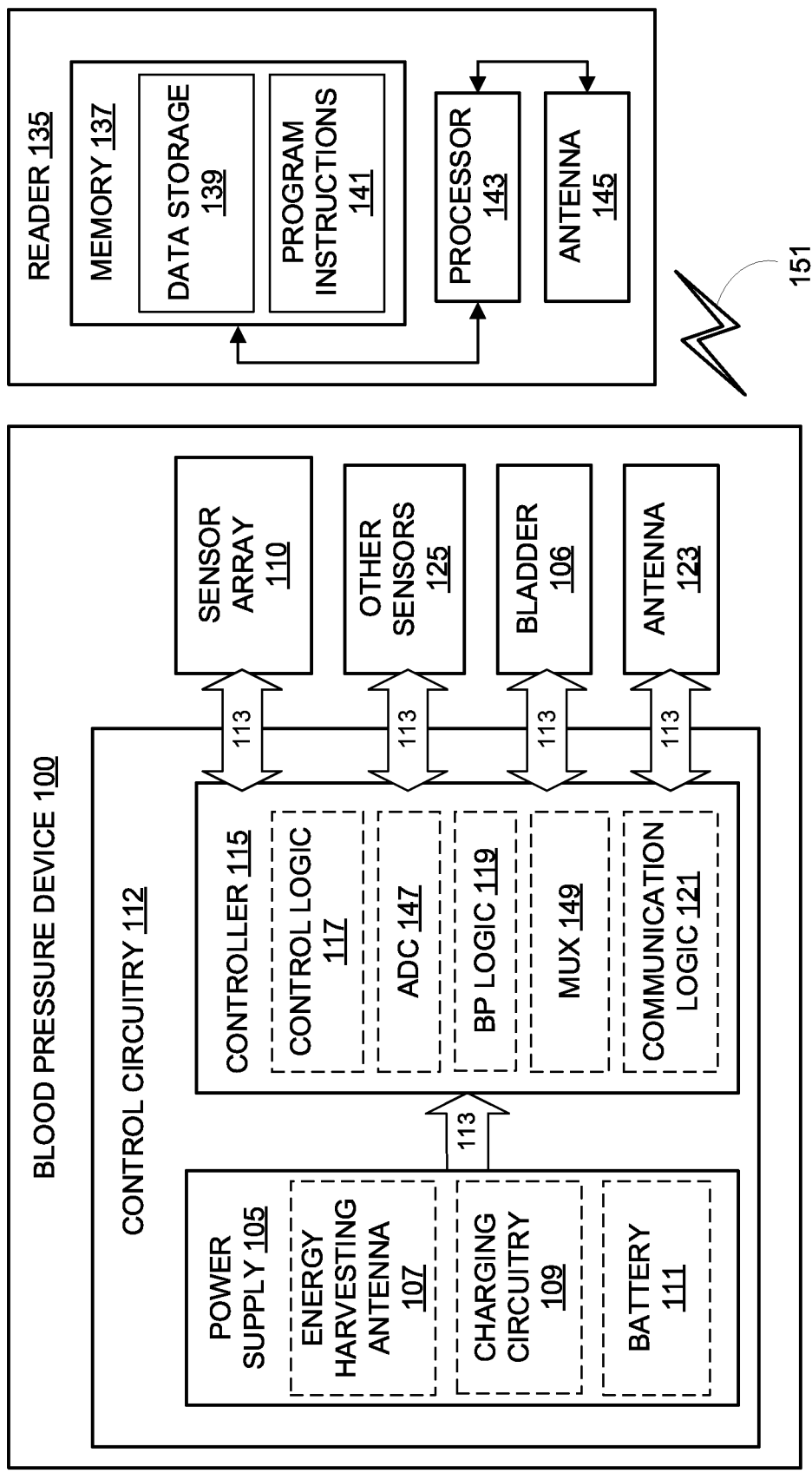
FIG. 1 is a functional block diagram of a blood pressure monitoring device, in accordance with an embodiment of the present disclosure.

Embodiments of a system and method for blood pressure estimation using a finger-wearable tactile sensor array are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

This disclosure enables convenient, nonintrusive, and painless blood pressure monitoring using a finger-wearable device. The finger-wearable device consists of a tactile sensor array to monitor and sense pressure applied to each of a plurality of sensors included in the tactile sensor array. The pressure applied to the tactile sensor array is due, at least in part, to artery pulsations and pressure applied via an actuation mechanism that consists of an inflatable bladder (e.g., an air bladder that is inflated with a pump, liquid-filled bladder, or any other bladder that is controllably expandable). This device is small, convenient and painless, enabling regular monitoring of blood pressure during the day as well as during sleep. Nocturnal monitoring of blood pressure is currently difficult, since traditional arm cuffs may awaken users by the compression of the arm. By contrast, this disclosure presents a finger-wearable blood pressure monitor device that can measure blood pressure with a reduced probability of awakening the user.

Furthermore, this disclosure presents embodiments of finger-wearable devices that utilize the monitoring and sensing of the tactile sensor array to automatically account for the fit of the finger-wearable device on a finger of a user. For example, a blood pressure estimation algorithm may account for discrepancies in measurements caused by a loose or tight fit around the finger of the user wearing the finger-wearable device. Tightness of fit may be automatically sensed by one or more sensors included in the tactile sensing array before inflation of the air bladder. In addition, the presence of multiple tactile sensing elements (e.g., each of the plurality of sensors) results in a plurality of tactile waveforms from the tactile sensor array that enables improved accuracy of blood pressure measurement and estimation.

Embodiments of the present disclosure utilize the finger-wearable device to monitor blood pressure in a digital artery, such as the digital artery on the ulnar or radial sides for example. The finger-wearable device may use oscillometry, auscultation, or applanation tonometry to estimate a user's blood pressure at the digital artery, which may subsequently be converted to a clinical or brachial blood pressure with a transfer function and machine learning algorithm. For applanation tonometry, the finger-wearable device may include a tactile sensor array that may be pressed into the finger over the digital artery, which may deform the digital artery. The digital artery may or may not be deformed to occlusion. As the pressure applied to tactile sensor array by the finger is slowly reduced, the digital artery may slowly convert back to a normal shape, and may pass through a point where the internal pressure equals the external pressure exerted on the digital artery by the tactile sensor array. This point may occur when a local radius of the digital artery approaches infinity, at least in reference to a size of a sensor of the tactile sensor array. In this state, e.g., with the local region of the digital artery being flat, the blood flow variations in the artery due to heart beats may cause the flat area of the digital artery to experience pressure fluctuations (e.g., arterial pulses). A maximum fluctuation, representing one of the arterial pulses having a pulse amplitude larger than the pulse amplitude of any other one of the arterial pulses, may occur at the flat condition, the pressure fluctuations may decrease when the local region is not quite flat. In some embodiments, the arterial pulse having a pulse amplitude greater than the pulse amplitude of any other arterial pulse included in all of the plurality of tactile waveforms is known as a basis arterial pulse. The basis arterial pulse is included in the arterial pulses occurs at a basis time instant and is included in the arterial pulses associated with a first tactile waveform included in the plurality of tactile waveforms. While the above operation was discussed in terms of a controlled reduction in pressure between the finger and the tactile sensor array, the operation may alternatively be performed using a controlled increase in pressure and the pressure changes may be measured during the controlled increase.

The tactile sensor array may include deformable capacitive sensors that may be deformed due to fluctuations in the arterial wall caused by the pressure fluctuations. These fluctuations may change a shape, e.g., height, of one or more deformable capacitive sensors, which may change their capacitance values. The changing capacitance may be measured, which provides an indication of the blood pressure in the digital artery. The capacitance levels of the capacitive sensors may be converted into pressure levels, e.g., mmHg, via a factory calibration procedure to form a plurality of tactile waveforms. Each of the plurality of tactile waveforms corresponding to the pressure applied to a respective one of the plurality of sensors over a first time period. Features of the plurality of tactile waveforms may be used to estimate a mean arterial pressure, a systolic blood pressure, and a diastolic blood pressure independently via regression modeling (e.g., a linear regression model such as Lasso) with a machine learning algorithm. In the same or other embodiments, a maximum amplitude of the measurement changes (e.g., capacitance changes) and/or pressure fluctuations of the plurality of sensors may be used to estimate a mean arterial pressure at the digital artery. Then, in some embodiments, the systolic and diastolic blood pressure at the digital artery may be estimated based on the mean arterial pressure.

To implement auscultation, the digital artery may be pressed to occlusion by the finger-wearable device then the pressure slowly reduced. A microphone included in the device may record sounds, known as Korotkoff sounds, originating in the digital artery as the blood begins to flow. The Korotkoff sounds change in character as the pressure applied to the artery is decreased. The applied pressure corresponding to the first Korotkoff sound may be an estimate of the systolic blood pressure, and the applied pressure corresponding to the termination of the Korotkoff sounds may be an estimate of the diastolic blood pressure.

To implement oscillometry, the digital artery may be pressed or squeezed by a bladder to a pressure at least above the systolic blood pressure, then the pressure may be slowly reduced. During the reduction in pressure, a pressure sensor measuring the pressure in the bladder may also measure pressure oscillations in the bladder due to blood flow in the digital artery. The pressure oscillations may start small, increase to a maximum amplitude, and reduce. Similar to the applanation tonometry technique, the applied pressure at maximum amplitude may be an estimate of the mean arterial pressure. From the measured pressure oscillations the mean arterial pressure, the systolic blood pressure, and the diastolic pressure may be estimated.

FIG. 1 is a functional blood diagram of blood pressure monitoring device 100, in accordance with an embodiment of the present disclosure. In the depicted embodiment, device 100 includes sensor array 110, control circuitry 112, other sensors 125, bladder 106, and antenna 123. The illustrated embodiment of control circuitry 112 includes a power supply 105 and a controller 115. The illustrated embodiment of power supply 105 includes an energy harvesting antenna 107, charging circuitry 109, and a battery 111. The illustrated embodiment of controller 115 includes control logic 117, blood pressure (BP) logic 119, Analog-to-Digital Converter (ADC) 147, multiplexer (MUX) 149, and communication logic 121. Furthermore, as illustrated, the various components of blood pressure device 100 are communicatively (e.g., electrically) coupled to each other via one or more interconnects 113.

Power supply 105 supplies operating voltages to the controller 115 and various other sensors and components of device 100. Antenna 123 is operated by controller 115 to communicate information to and/or from device 100. In the illustrated embodiment, antenna 123, controller 115, and power supply 105 are disposed on a substrate (e.g., substrate 208 illustrated in FIG. 2A).

In the illustrated embodiment, power supply 105 includes battery 111 to power the various embedded electronics, including controller 115. Battery 111 may be inductively charged by charging circuitry 109 and energy harvesting antenna 107. In one embodiment, antenna 123 and energy harvesting antenna 107 are independent antennae, which serve their respective functions of energy harvesting and communications. In another embodiment, energy harvesting antenna 107 and antenna 123 are the same physical antenna that are time shared for their respective functions of inductive charging and wireless communications with reader 135. In yet other embodiments, battery 111 may be charged via a wire plugged into device 100.

Charging circuitry 109 may include a rectifier/regulator to condition the captured energy for charging battery 111 or directly power controller 115 without battery 411. Charging circuitry 109 may also include one or more energy storage devices to mitigate high frequency variations in energy harvesting antenna 107. For example, one or more energy storage devices (e.g., a capacitor, an inductor, etc.) can be connected to function as a low-pass filter.

Controller 115 contains logic to choreograph the operation of the other embedded components. Control logic 117 controls the general operation of device 100, including providing a logical user interface, power control functionality, etc. Additionally, control logic 117 controls the inflation and deflation of bladder 106 and receives pressure data from a pressure sensor included in the bladder 106. ADC 147 may receive data from other sensors 125 and sensor array 110. ADC 147 may convert the received data to a digital format and provide the same to control logic 117 and/or BP logic 119. In some embodiments, ADC 147 may be coupled to sensor array 110 and the other sensors 125 via MUX 149, which controls the inflow of data to the ADC 147.

BP logic 119 may receive the measurements (e.g., capacitance measurements) from the sensor array 110 and convert the measurements into equivalent pressure values. The pressure values may be in mmHg, for example. The pressure values may further be converted into pressure waveforms (e.g., a plurality of tactile waveforms) for each sensor included in sensor array 110 that may be analyzed in either the time or frequency domains to determine mean arterial pressure, systolic blood pressure, and/or diastolic blood pressure at the digital artery, in accordance with embodiments of the disclosure. In some embodiments, the plurality of tactile waveform may be converted from a first waveform (e.g., pressure at the digital artery) type to a second waveform type (e.g., pressure at a brachial artery). BP logic 119 (and other components) may analyze the plurality of tactile waveforms to determine arterial pulses for each of the plurality of tactile waveforms. Each of the plurality of tactile waveforms having a corresponding one of the arterial pulses having a maximum pulsatile amplitude (e.g., an arterial pulse having a local maximum amplitude within a particular tactile waveform included in the plurality of tactile waveforms). The determined arterial pulses may subsequently be utilized to estimate blood pressure.

In some embodiments, BP logic 119 may receive sound recordings from a microphone to implement auscultatory blood pressure estimation. The microphone may be part of other sensors 125, which may be arranged to record blood pulses occurring in the digital artery. BP logic 119 may analyze the sound recordings in relation to pressure data received from bladder 106 (due to the pressure sensor included in bladder 106) to determine a pressure when Korotkoff sounds begin and end. If the pressure in bladder 106 is decreasing during this time, the pressure corresponding to the beginning of the Korotkoff sounds may be an estimate of the systolic blood pressure, whereas the pressure corresponding to the ending of the Korotkoff sounds may be an estimate of the diastolic blood pressure.

In some embodiments, BP logic 119 may determine the mean arterial pressure (MAP), systolic blood pressure (SBP), and diastolic blood pressure (DBP) using oscillometry. The determination of the mean arterial pressure, systolic blood pressure, and diastolic blood pressure may be similar to the applanation tonometry techniques but the pressure sensor measurements within bladder 106 may be used instead of the measurements of tactile sensor array 110. For example, the pressure sensor included in bladder 106 may measure pressure changes due to blood flow in the digital artery pressing the finger on bladder 106. The pressure corresponding to when a maximum amplitude of an arterial pulse may be an estimate of the mean arterial pressure. Subsequently, BP logic 119 may determine the systolic blood pressure and diastolic blood pressure through one or more regressions (e.g., linear regression), in accordance with an embodiment of the disclosure.

In some embodiments, BP logic 119 may perform BP estimations using all three techniques. The BP estimations from the three different techniques may then be compared to determine a closest estimation of the user's BP at the digital artery. Additionally, or alternatively, BP logic 119 may utilize the blood pressure estimates from the oscillometry and auscultatory techniques as reference data to confirm and/or verify the accuracy of the blood pressure estimate from tactile sensor array 110 determined with regularized regression modeling of the machine learning algorithm.

Control logic 117 may receive diagnostic data from other sensors 106, which may include a temperature sensor, accelerometer, photoplethysmograph (PPG), and microphone. The data may be analyzed to determine if any of the measurements are outside of established thresholds and, if so, response accordingly. For example, if accelerometer data shows that the finger was moving more than desired during a blood pressure reading, control logic 117 may reject that reading. Additionally, control logic 117 may determine the user's heart rate (HR), respiratory rate (RR), and/or oxygen saturation (SpO2) based on PPG sensor data. Lastly, temperature data may be used to adjust any blood pressure estimations if the temperature is outside of an established range.

Communication logic 121 provides communication protocols for wireless communication with reader 135 via antenna 123. In one embodiment, communication logic 121 provides backscatter communication via antenna 123 when in the presence of an electromagnetic field 151 output from reader 135. In one embodiment, communication logic 121 operates as a smart wireless radio-frequency identification ("RFID") tag that modulates the impedance of antenna 123 for backscatter wireless communications. The various logic modules of controller 115 may be implemented in software/firmware executed on a general purpose microprocessor, in hardware (e.g., application specific integrated circuit), or a combination of both.

The illustrated embodiment also includes reader 135 with a processor 143, an antenna 145, and memory 137. Memory 137 includes data storage 139 and program instructions 141. As shown reader 135 may be disposed outside of device 100, but may be placed in its proximity to charge device 100, send instructions to device 100, and/or extract data from device 100. In one embodiment, reader 135 may resemble a hand held portable device that provides a holder or case for device 100.

External reader 135 includes antenna 145 (or group of more than one antenna) to send and receive wireless signals 151 to and from device 100. External reader 135 also includes a computing system with processor 143 in communication with memory 137. Memory 137 is a non-transitory computer-readable medium that can include, without limitation, magnetic disks, optical disks, organic memory, and/or any other volatile (e.g., RAM) or non-volatile (e.g., ROM) storage system readable by the processor 143. Memory 137 can include a data storage 139 to store indications of data, such as data logs (e.g., user logs), program settings (e.g., to adjust behavior of device 100 and/or external reader 135), etc. Memory 137 can also include program instructions 141 for execution by processor 143 to cause the external reader 135 to perform processes specified by the instructions 141. For example, program instructions 141 can cause external reader 135 to provide a user interface that allows for retrieving information communicated from device 100 or allows transmitting information to device 100 to program or otherwise select operational modes of device 100. External reader 135 can also include one or more hardware components for operating antenna 145 to send and receive wireless signals 151 to and from device 100.

External reader 135 can be a smart phone, digital assistant, or other portable computing device with wireless connectivity sufficient to provide wireless communication link 151. External reader 135 can also be implemented as an antenna module that can be plugged into a portable computing device, such as in an embodiment where wireless communication link 151 operates at carrier frequencies not commonly employed in portable computing devices. In some embodiments, external reader 135 may prompt a user of device 100 to prepare for a BP reading, which may provide the user a moment to position the finger at an elevation equal with their heart. Additionally, while the BP reading is being performed, external reader 135 may provide a distraction to the user. For example, the distraction could take the form of a news article, current weather conditions, a game, or display heart beat waveforms and BP measurements.

Figure 2B:
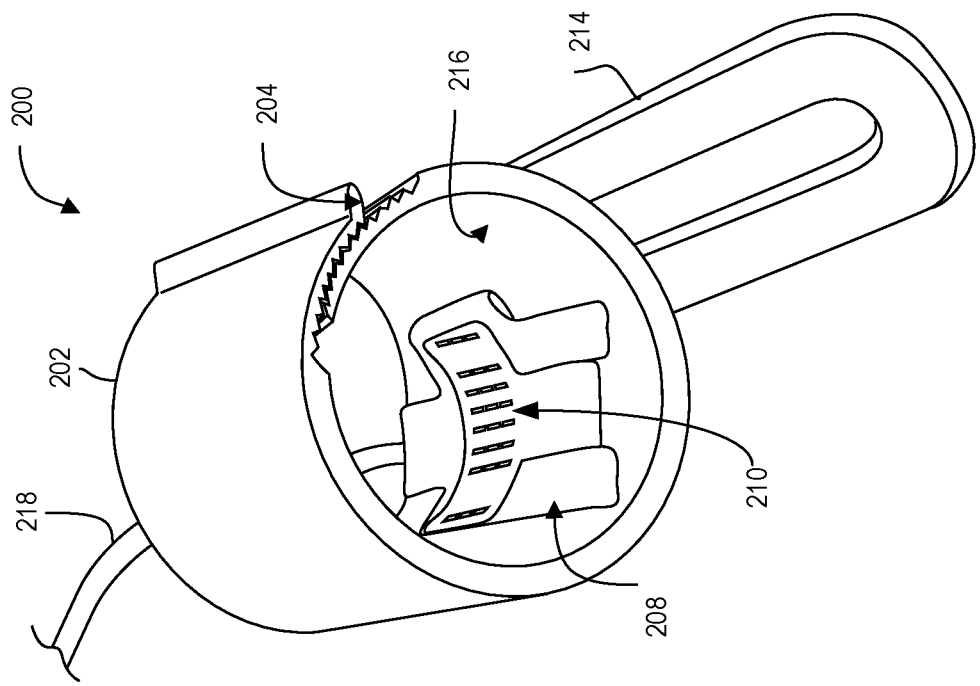
FIG. 2B illustrates a perspective view of the finger-wearable blood pressure monitor device, in accordance with an embodiment of the present disclosure.
Figure 2A:
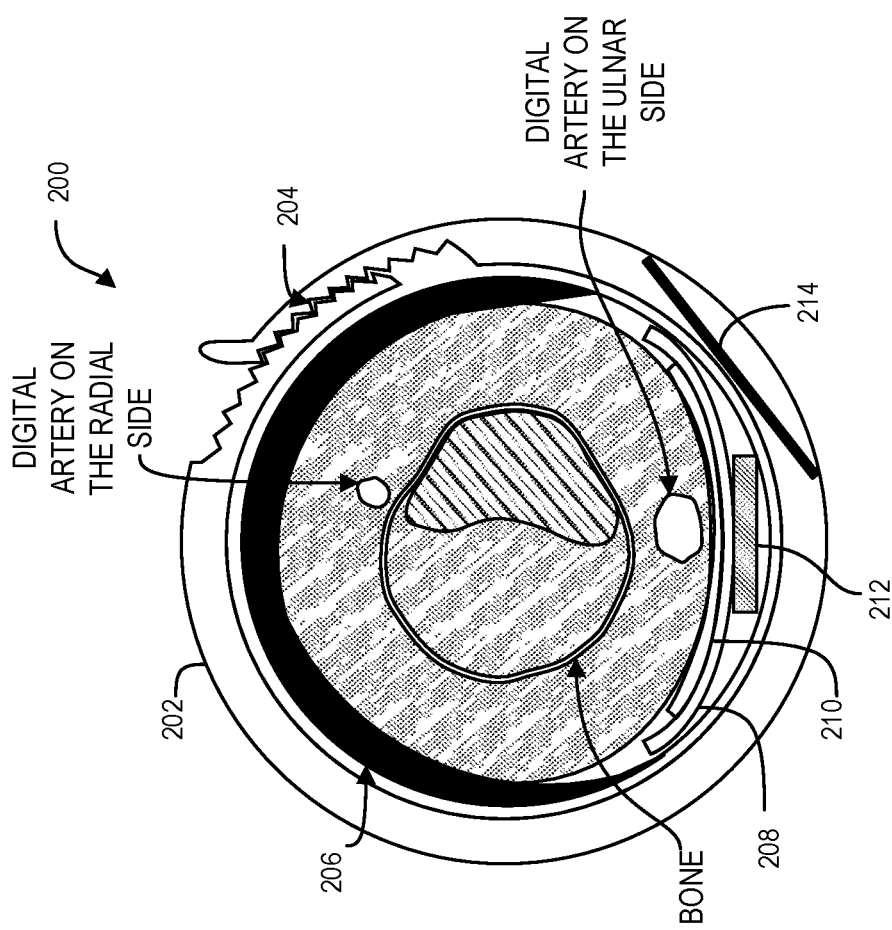
FIG. 2A illustrates a cross-sectional view of a finger-wearable blood pressure monitoring device, in accordance with an embodiment of the present disclosure.

FIGS. 2A-2B illustrates two views of finger-wearable blood pressure monitoring device 200. Device 200 is one possible implementation of blood pressure monitoring device 100 illustrated in FIG. 1. The illustrated embodiment of finger-wearable blood pressure monitoring device 200 includes a cuff 202 (with an inward facing surface 216), a size adjustment mechanism 204, a bladder 206, a substrate 208, a tactile sensor array 210, control circuitry 212, an alignment tab 214, and an electrical connection 218. Cuff 202 has an annular shape (e.g., ring or disk shaped) to fit over a finger of the user. In some embodiments, cuff 202 may wrap around the finger of the user. In other embodiments, cuff 202 may have a solid annular shape (e.g., such as a ring with an extended width) that slides onto the finger of the user.

Finger-wearable blood pressure monitoring device 200, device 200 for short, may be worn or engaged with a digital artery, e.g., an artery of a finger, to determine the blood pressure of a user, along with other diagnostic data. In some embodiments, the other diagnostic data may include heart rate (HR), respiratory rate (RR), temperature, and blood oxygen saturation (SpO2). In some embodiments, motion of device 200 may also be detected. Device 200 may be worn on the finger of the user throughout the day, night, both, or periodically to monitor the user's blood pressure. In some embodiments, device 200 may provide the blood pressure readings and the other diagnostic data/movement data to an external reader (e.g., external reader 135 of FIG. 1). In turn, the external reader may record the data, alert the user and/or user's physician to readings outside of designated ranges, or transmit the data to an electronic medical record associated with the user, for example.

Device 200 may be worn on the finger with tactile sensor array 210 oriented to align with the digital artery of the finger. In some embodiments, the tactile sensor array 210 may be aligned 60° to the palm so that tactile sensor array 210 is centered over the digital artery on the ulnar side of the finger. The size adjustment mechanism 204 may be adjusted to ensure a snug fit around the finger. In some embodiments, the bladder 206 may be dynamically inflated to ensure that the digital artery and the tactile sensor array 210 are pressed together. Subsequently, tactile sensor array 210 may monitor, measure, and/or sense pressure applied, over a first time period, to each of the plurality of sensors included in tactile sensor array 210. The pressure applied to tactile sensor array 210 includes pressure fluctuation (e.g., arterial pulses) caused by blood flow in the digital artery. Device 200 may subsequently convert the monitored, measured, and/or sensed pressure into a mean arterial pressure, a systolic blood pressure, and/or a diastolic blood pressure, in accordance with embodiments of the present disclosure. In some embodiments, control circuitry 212 may perform the conversion. In other embodiments, data representing the monitored, measured, and/or sensed pressure may be transmitted, via wire or wirelessly, to an external reader for the conversion process. While device 200 includes bladder 206 to facilitate applying the pressure, in other embodiments, the bladder may be omitted and the size adjustment mechanism 204 may be adjusted to provide the necessary pressure.

Bladder 206 may be disposed on an inward facing surface 216 of cuff 202 and, in some embodiments, may be disposed along a majority of the inner circumference of cuff 202. In some embodiments, the bladder 206 may generally be disposed on a portion of inward facing surface 216 opposite from the location of tactile sensor array 210, which is disposed on or adjacent to inward facing surface 216. Bladder 206 may be formed from a soft, flexible material and may inflate (e.g., enlarge and/or stretch) due to an increase in internal pressure. In some embodiments, air may be introduced, e.g., pumped, in bladder 206 to cause bladder 206 to expand to facilitate measurements with tactile sensor array 210.

Substrate 208 may provide a mounting surface for tactile sensor array 210 and/or control circuitry 212. Substrate 208 may be formed from a rigid material, such as plastic, ceramic, or metal, and may be disposed on the inward facing surface 216 of cuff 202.

Tactile sensor array 210 may be a sensor array formed from a plurality of individual sensors (e.g., capacitive sensors). Tactile sensor array 210 may be disposed on substrate 208 and arranged to be in contact with the finger of the user. The plurality of sensors may be arranged into a two-dimensional array comprising a number of columns and a number of rows. In some embodiments, the columns may be arranged to align longitudinally with the finger and the rows align circumferentially. Of course, the opposite arrangement of the columns and rows may be implemented. In some embodiments, there may be more columns than rows to ensure tactile sensor array 210, or at least a column of sensors, is centered over the digital artery area of the finger. In general, it may be desirable to have at least one sensor of tactile sensor array 210 contact the skin directly above the digital artery so that pressure fluctuations of the applied pressure to tactile sensor array 210 by the digital artery may be measured as changes (e.g., in capacitance) of the at least one sensor.

For example, one or more individual sensors of tactile sensor array 210 may be aligned with the digital artery and may detect changes in the pressure applied and/or the pressure fluctuations caused by the digital artery to the corresponding sensor of tactile sensor array 210. The detection of these changes may be due to the sensor deforming in response, which indicate blood flow and blood pressure. The detected changes in the pressure applied and/or the pressure fluctuations, which cause a change in the reading of one or more of the sensors include in tactile sensor array 210, may be converted into mean arterial pressure, systolic blood pressure, and/or diastolic blood at the digital artery, in accordance with embodiments of the present disclosure.

Control circuitry 212 may be coupled to choreograph the operation of the device 200, and may be disposed between inward facing surface 216 of the cuff 202 and substrate 208. In some embodiments, control circuitry 212 may be disposed on a side of substrate 208 facing the inward facing surface 216 of the cuff 202. In other embodiments, control circuitry 212 may be disposed on the inward facing surface 216 of cuff 202 underneath substrate 208. Control circuitry 212 may be coupled to tactile sensor array 210 to receive measurement readings (e.g., capacitance), and may be further coupled to bladder 208 to control inflating and deflating. Additionally, control circuitry 212 may be coupled via a wire or wirelessly to an external reader for providing and receiving data and/or power.

Alignment tab 214 may assist the user in aligning tactile sensor array 210 to a desired digital artery. For example, alignment tab 214 may be aligned with the palm so that tactile sensor array 210 may be aligned with the digital artery.

In operation, device 200 may detect and monitor the user's BP, along with the various other diagnostic variables. In some embodiments, device 200 may analyze the readings of each sensor in the plurality of sensors of tactile sensor array 210 via regression modeling to determine the user's BP. In other embodiments, applanation tonometry may be used determine the user BP at the digital artery, which may then be transformed into a brachial BP measurement. In yet other embodiments, device 200 may implement oscillometry and/or auscultation to monitor the BP in the digital artery. In general, bladder 106 may be inflated to cause the finger to press onto tactile sensor array 210, then bladder 206 may be deflated. During either the inflation or the deflation of bladder 206 over a first time period, tactile sensor array 210 may monitor, measure, and/or sense pressure applied to tactile sensor array by the digital artery of the finger. The pressure may include pressure fluctuations (e.g., arterial pulses) caused by blood flow within the digital artery. The monitored, measured, and/or sensed pressure may be converted into blood pressure estimations. For example, bladder 206 may be inflated in a slow, controlled manner, and the arterial pulses may be determined when the tactile sensor array 210 is being slowly pressed into the digital artery. Alternatively or additionally, the arterial pulses may be measured during a slow, controlled deflation of bladder 206, which may allow for the pressure applied to tactile sensor array 210 by the digital artery to slowly decrease. In either operation, tactile sensor array 210 may create a condition on or at the arterial wall of the digital artery that allows applanation tonometry to be performed, e.g., when a local radius of curvature of the digital artery approaches infinity, at least compared to a size of a sensor included in tactile sensor array 210. While the detailed operation of device 200 may be described in terms of deflation of bladder 206, the same principles of operation may be applied during a slow, controlled inflation of bladder 206.

In some embodiments, blood pressure is estimated based on regression modeling with a machine learning algorithm. Device 200 may monitor, over a first time period, the pressure applied to each of the plurality of sensors by the digital artery of the finger. The pressure applied may include pressure fluctuations representative of arterial pulses due to blood flow within the digital artery. In response to monitoring the pressure, device 200 generates a plurality of tactile waveforms that each corresponds to the pressure applied to a respective one of the plurality of sensors over the first time period. Subsequently, device 200 may utilize, at least in part, the plurality of tactile waveforms to estimate blood pressure. For example, the plurality of tactile waveforms may be decomposed by one or more filters into a lowpass component and a bandpass component. The lowpass component is representative of the pressure applied over the first time period with some amount of high frequency content (e.g., some or all of the pressure fluctuations) filtered out. The bandpass component is representative of the pressure fluctuations over the first time period. From the bandpass component, device 200 detects arterial pulses for each of the plurality of tactile waveforms.

In the same or other embodiments, at least one comparison metric based on at least one of the plurality of tactile waveforms will be determined and subsequently utilized to determine whether to accept or reject at least one of the plurality of tactile waveforms. For example, for each of the plurality of tactile waveforms, device 200 may then identify one (e.g., a maximum amplitude arterial pulse) of the arterial pulses having a pulse amplitude greater than the pulse amplitude of any other one of the arterial pulses included in a corresponding tactile waveform included in the plurality of tactile waveform. In other words, each of the maximum amplitude arterial pulses is an arterial pulse that represents a local maximum amplitude of the arterial pulses corresponding one of the plurality of tactile waveforms. The maximum amplitude arterial pulse may be compared to a pulse amplitude threshold to determine whether to reject or accept individual tactile waveforms included in the plurality of tactile waveforms. This comparison may allow for systematically removing some of the tactile waveforms corresponding to outliers in the plurality of tactile waveforms.

In some embodiments, a first set of tactile waveforms included in the plurality of tactile waveforms may be determined by comparing the maximum amplitude arterial pulse of each of the plurality of tactile waveforms to the pulse amplitude threshold. Then, a temporal spread metric based on time instants of the maximum amplitude arterial pulse of the first set of tactile waveforms may subsequently be determined. The temporal spread metric of the first set of tactile waveforms may be compared to the temporal spread threshold to determine whether to accept or reject the plurality of tactile waveforms.

In other embodiments, the maximum amplitude arterial pulse may not necessarily have the maximum pulse amplitude of the particular tactile waveform or may include several arterial pulses. For example, the maximum amplitude arterial pulse may have a second or third largest pulse amplitude relative to other arterial pulses in the corresponding one of the plurality of tactile waveforms. Several arterial pulses may be determined to be the maximum amplitude arterial pulse in some situations in which more than one of the arterial pulses of a particular tactile waveform has a pulse amplitude above a maximum amplitude threshold value. A mean arterial pressure may be determined based on the maximum amplitude arterial pulse of the plurality of tactile waveforms. The determined mean arterial pressure may be compared to a reference measurement (e.g., a reference mean arterial pressure determined by summing one third of a reference systolic blood pressure measurement and two thirds of reference a diastolic blood pressure measurement) to determine whether to accept the plurality of tactile waveforms as a valid measurement.

Device 200 compares the maximum amplitude arterial pulses to threshold values to determine whether to accept or reject the plurality of tactile waveforms as valid measurements. For example, valid measurements may be utilized to estimate blood pressure, while invalid measurements may be attributed to error during the measurement. After deciding which of the plurality of tactile waveforms should be considered valid, features are then extracted from the lowpass component and the bandpass component of the remaining plurality of tactile waveforms (e.g., the tactile waveforms determined to be valid measurements). These features may be at various time instants and pressure values of the lowpass component and the bandpass component. A machine learning algorithm is then developed based on a regularized regression model, such as Lasso, of the features to estimate mean arterial pressure, systolic blood pressure, and diastolic blood pressure independently. The model to estimate blood pressure may be generated, at least in part, by comparing measured data (e.g., training data) to reference data (e.g., training examples). In the same or other embodiments, device 200 may determine the blood pressure using applanation tonometry, such as a mean arterial pressure. Mean arterial pressure may subsequently be used to determine systolic blood pressure and diastolic blood pressure. For example, control circuitry 212 may cause bladder 206 to inflate to a pressure that is at least above the systolic blood pressure of the user.

In some embodiments, bladder 206 may be inflated until occlusion of the digital artery. Inflating to occlusion, however, may not be necessary, but may be performed when device 200 is initially used to ensure the pressure is above the systolic blood pressure. To determine if occlusion is reached, tactile sensor array 210 may monitor for pressure changes via sensor measurements. Once bladder 206 has been inflated to the desired pressure, control circuitry 212 may deflate bladder 206 at a slow and controlled rate. For example, bladder 206 may be deflated at a rate of 2 to 3 mmHg per second. While bladder 206 is deflating, tactile sensor array 210 may measure the pressure (included the pressure fluctuations) applied to tactile sensor array 210 by the digital artery. As the pressure exerted by bladder 206 decreases, the external pressure on the digital artery will decrease. The decrease in the external pressure on the digital artery affects the differential between the external pressure on the artery and the internal pressure on the artery. As these two pressures tend toward being equal, at which time the arterial wall may be flat at least in regards to the sensor of tactile sensor array 210, the arterial pulses due blood flow from the heartbeat begin to show a change as detected by tactile sensor array 210. The changes may appear as pulsatile waveforms or fluctuations in the measurements/levels (e.g., capacitance measurements) of tactile sensor array 210. The pressure at which a maximum amplitude occurs in a pulsatile waveform may be the mean arterial pressure, which may be indicative of the user's blood pressure in the digital artery. However, as discussed in the present disclosure, regression modeling may also be utilized to estimate mean arterial pressure that does not rely on a maximum amplitude of a particular pulsatile waveform. After detection of mean arterial pressure, control circuitry 212 may provide the data to an external reader for algorithmic manipulation to extract systolic blood pressure and diastolic blood pressure from the mean arterial pressure, or control circuitry 212 may estimate the mean arterial pressure, systolic blood pressure, and diastolic blood pressure.

Figure 3A:
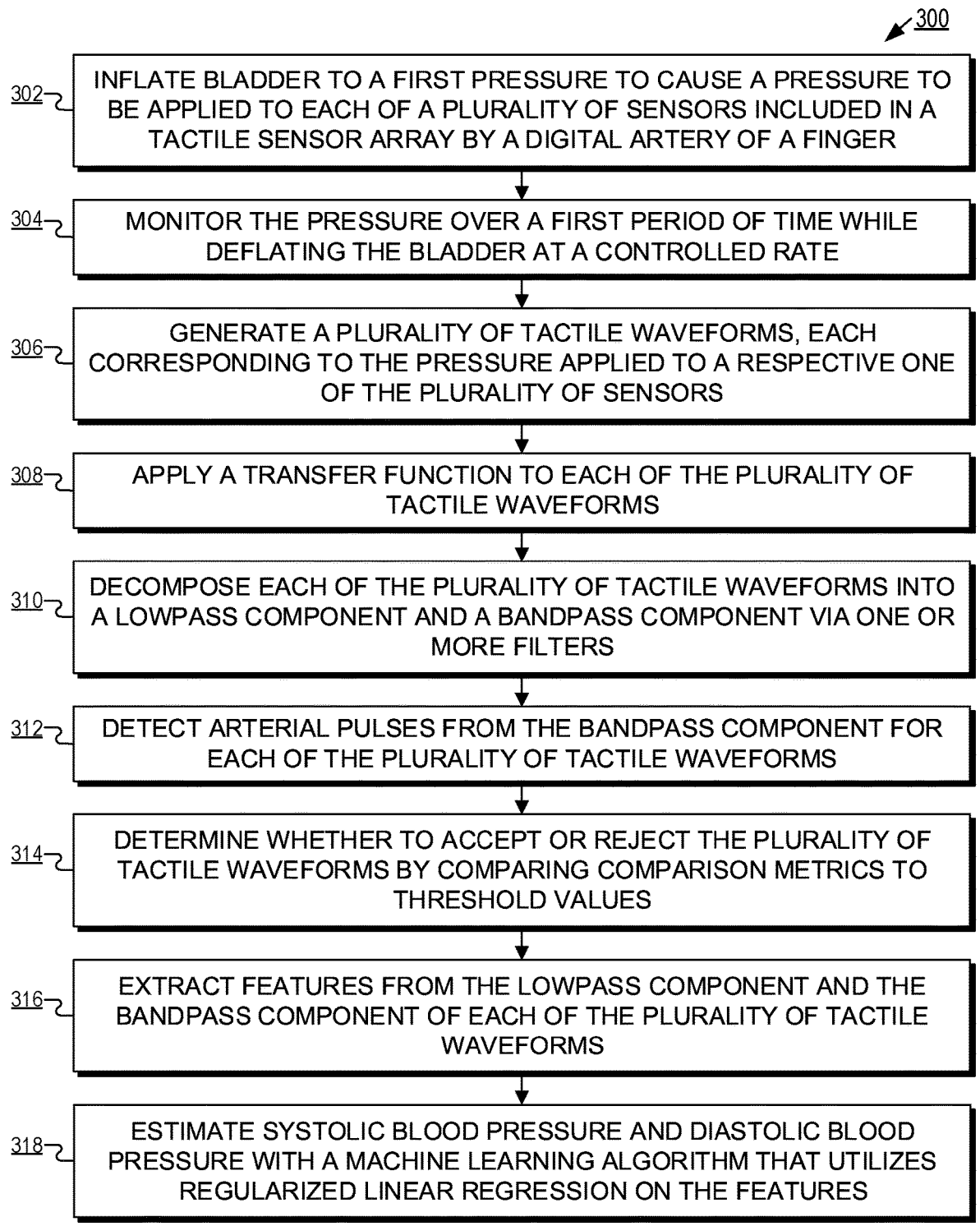
FIGS. 3A-3B illustrate a method for estimating blood pressure, in accordance with an embodiment of the disclosure.
Figure 3B:
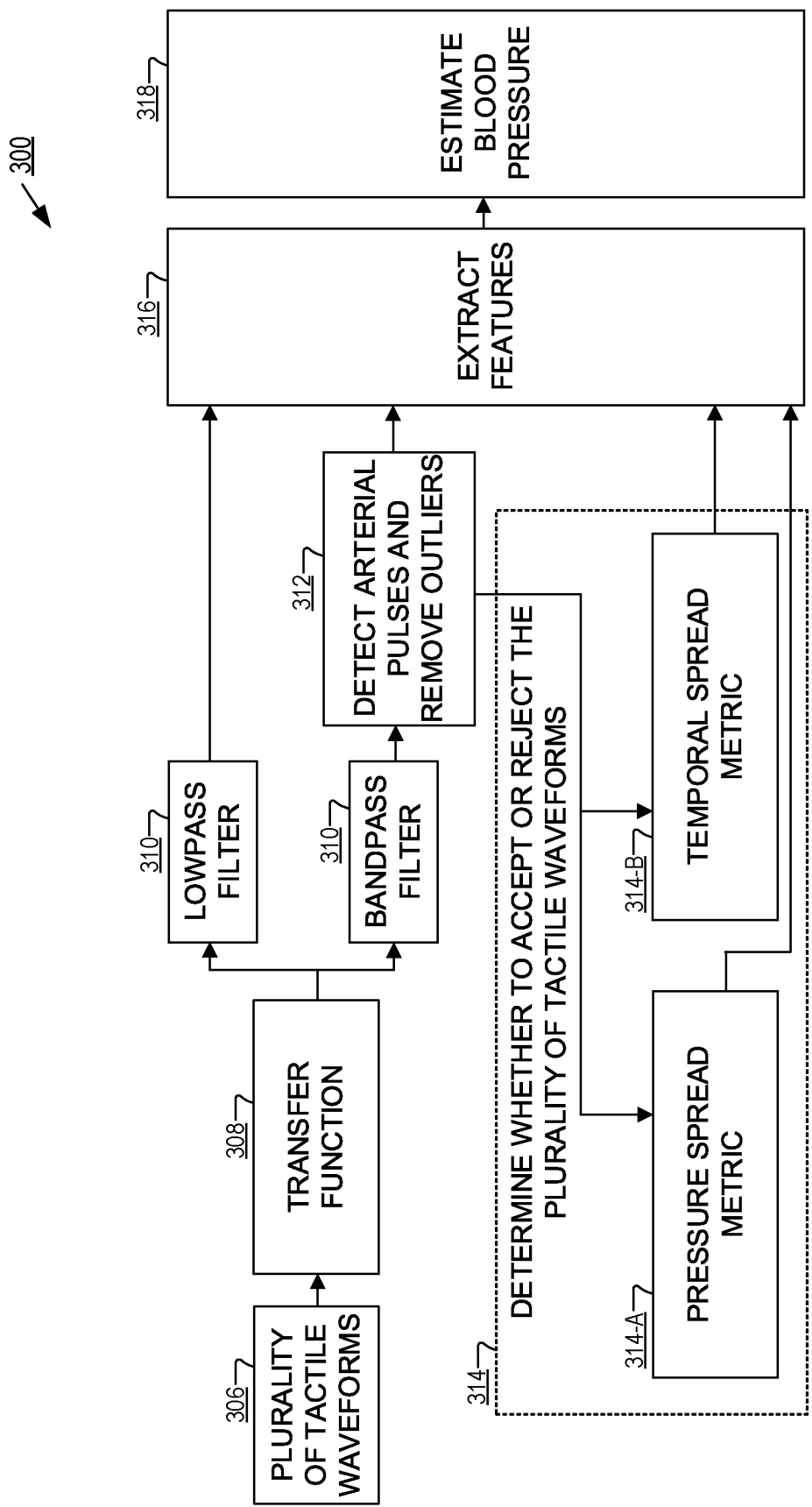

FIGS. 3A-3B illustrate method 300 for estimating blood pressure, in accordance with an embodiment of the disclosure. Method 300 may be an example operation of device 100 and/or device 200. Method 300 outlines some of the steps in estimating blood pressure using a finger-wearable blood pressure monitoring device using regression modeling with a machine learning algorithm. In some embodiments, the device may implement applanation tonometry to determine the blood pressure. In other embodiments, oscillometry or auscultation may be implemented in addition to or instead of the applanation tonometry. While the method 300 is discussed in terms of slowly deflating the bladder to determine the blood pressure at the digital artery, the method 300 may also be used during a slow, controlled inflation of the bladder, or without the bladder entirely.

Method 300 may begin at step 302 with inflating a bladder of a finger-wearable blood pressure monitoring device to a first pressure to cause a pressure applied to each of a plurality of sensors including in a tactile sensor array. Inflating the bladder may cause a finger of a user to be pressed onto the tactile sensor array of the finger-wearable blood pressure monitoring device. In some embodiments, the first pressure may be a pressure at least greater than a systolic blood pressure of the user. In other embodiments, the first pressure may be high enough to occlude blood flow in a digital artery of the finger.

Step 302 may be followed by step 304, which includes monitoring the pressure over a first time period while deflating the bladder at a controlled rate once reaching the first pressure. In some embodiments, the bladder may be deflated at a rate of 2 to 3 mmHg/s. Monitoring the pressure may include determining changes (e.g., capacitance level) of one or more sensors included in the tactile sensor array. The changes are indicative of the applied pressure and pressure fluctuations (e.g., arterial pulses) caused by blood flow within the digital artery of the finger.

Step 304 may be followed by step 306, which includes based on the monitoring the pressure over the first time period, generating a plurality of tactile waveforms. Each of the plurality of tactile waveforms corresponds to the monitored pressure (e.g., capacitance level changes) over the first time period of a respective one of the plurality of sensors included in the tactile sensor array.

Step 306 may be followed by step 308, which includes applying a transfer function to each of the plurality of tactile waveforms to convert/map each of the plurality of tactile waveforms from a first waveform (e.g., pressure at the digital artery) type to a second waveform type (e.g., pressure at a brachial artery). Then for example, the plurality of tactile waveforms may be used to estimate blood pressure at various arterial positions.

Step 308 may be followed by step 310, which includes decomposing each of the plurality of tactile waveforms into a lowpass component and a bandpass component via one or more filters (e.g., a lowpass filter and a bandpass filter). The bandpass component corresponds to pressure fluctuations (e.g., arterial pulses) over the first time period. The pressure fluctuations over the first time period are due, at least in part, to blood flow within the digital artery of the finger. The lowpass component corresponds to the pressure applied over the first time period without at least some of the pressure fluctuations. In other words, decomposing each of the plurality of tactile waveforms allows for assessment and characterization of different frequency components of each of the plurality of tactile waveforms. In some embodiments, the lowpass component may be representative of a portion of the plurality of tactile waveforms having a frequency lower than a predetermined cut-off frequency. Similarly, the bandpass component may be representative of a portion of the plurality of tactile waveforms within a certain frequency range.

Step 310 may be followed by step 312, which includes detecting arterial pulses (e.g., based on the pressure fluctuations) from the bandpass component for each of the plurality of waveforms. Isolating the bandpass component will also provide for a relatively unobstructed view of pulsatile pressure with respect to time. Pulsatile pressure shows the periodic change in the pressure over the first time period from, at least in part, the pressure fluctuations due to blood flow within the digital arterial of the finger. Thus, by determining the duration between peaks and valleys of each periodic event (e.g., individual arterial pulses included in the arterial pulses) in the bandpass region, a pulse and/or heart rate of the user can be estimated. Additionally, a pulse amplitude of each of arterial pulses may be determined, including determining which one of the arterial pulses has a pulse amplitude greater than any other one of the arterial pulses for a corresponding one of the plurality of tactile waveforms. The particular arterial pulse having the greater pulse amplitude relative to all other arterial pulses in the corresponding one of the plurality of tactile waveforms corresponds to a maximum amplitude arterial pulse. Each of the plurality of tactile waveforms has a particular arterial pulse corresponding to the maximum amplitude arterial pulse.

Step 312 may be followed by step 314, which includes determining whether to accept or reject the plurality of tactile waveforms as a valid measurement by comparing comparison metrics based on the plurality of tactile waveforms to threshold values. It may be desirable to remove outliers (e.g., individual tactile waveforms included in the plurality of tactile waveforms) which may disrupt any potential fit of the plurality tactile waveforms. Disruption of any potential fit may lead to inadvertent error reducing the effectiveness of estimating blood pressure. The threshold values may include at least one of a median absolute deviation pressure threshold, a temporal spread threshold, or a pulse amplitude threshold.

For example, erratic waveforms caused by swollen joints and/or improper fit of the cuff may cause high element pressure spread between individual sensors within the tactile sensor array. The comparison metric may include at least the maximum amplitude arterial pulse. The maximum amplitude arterial pulse for each of the plurality of tactile waveforms may be compared to a pulse amplitude threshold to determine whether the corresponding tactile waveform is an outlier. A first set of the tactile waveforms included in the plurality of tactile waveforms may be identified based on the comparison between the maximum amplitude arterial pulse and the pulse amplitude threshold. A temporal spread metric based on time instants of the maximum amplitude arterial pulse of the first set of tactile waveforms may then be determined. The temporal spread metric may then be compared to a temporal spread threshold to determine whether the all of the plurality of tactile waveforms are valid measurements.

Several other data rejection of measurement values may be desired. For example, a basis arterial pulse may be identified as having a pulse amplitude greater than any other arterial pulse included in all of the plurality of tactile waveforms. The basis arterial pulse is at a basis time instant during the first time period. The lowpass component at the basis time instant for each of the plurality of tactile waveforms may be utilized to determine a pressure spread metric. The pressure spread metric may then be compared to a pressure spread threshold to determine whether to accept or reject the plurality of tactile waveforms.

In other embodiments, the basis arterial pulse may be compared to a reference measurement (e.g., a reference mean arterial pressure of the same patient performed during calibration). The basis arterial pulse may then be compared to the threshold values to determine whether to accept or reject the plurality of tactile waveforms as valid. In other words, the sensor included in the tactile sensor array with an arterial pulse corresponding to an ideal or near ideal mean arterial pressure is determined and compared to the reference measurement (e.g., training examples). This may be the sensor that provides the closest mean arterial pressure estimate at the basis time instant to a reference on training data. The mean arterial pressure reference may be a third of the reference systolic blood pressure plus two thirds of the reference diastolic blood pressure rather than being a direct measurement of mean arterial pressure. Then for a desired transfer function, a threshold value such as one of a median absolute deviation pressure threshold, temporal spread threshold, or pulse amplitude threshold is determined to be used for comparison to comparison metrics derived from the plurality of tactile waveforms. To reduce standard of deviation of mean arterial pressure error in training data, a target data rejection percentage is provided to further determine the threshold values.

Additional threshold values may also be used. For example, the plurality of tactile waveforms may be determined to be invalid if reference auscultatory measurements differ by greater than 4 mmHg, reference auscultatory measurements vary by greater than 12 mmHg (systolic) or 8 mmHg (diastolic) across consecutive trials for the same user, user has an irregular heartbeat as determined by a study nurse, pressure spread is greater than a pressure spread threshold, temporal spread is greater than a temporal spread threshold, or a low number of (e.g., less than 3) sensors included in the tactile sensor array have a pulse amplitude greater than or equal to a pulse amplitude threshold (e.g., 3 mmHg).

Step 314 may be followed by step 316, which includes extracting features from the lowpass component and the bandpass component of the plurality of tactile waveforms (e.g., the tactile waveforms included in the plurality of tactile waveforms not removed as outliers and/or that met the desired threshold requirements). The features are characteristic aspects of the plurality of tactile waveforms that can be utilized for generating a model for estimating blood pressure. For example, the features may be determined based on feature time instants identified, at least in part, by the basis arterial pulse. The basis arterial pulse was previously described as the arterial pulse having a pulse amplitude greater than the pulse amplitude of any other one of the arterial pulses included in all of the plurality of tactile waveforms. The basis arterial pulse occurs at the basis time instant included in a first tactile waveform of the plurality of tactile waveforms. Feature time instants may then be determined by computing a feature curve versus time that fits pulse amplitudes of the arterial pulses included in the bandpass component of the first tactile waveform during the first time period. The feature time instants are within the first time period where there is at least one of a maximum pulse amplitude, maximum slope, minimum slope, and/or a foot of the feature curve. The features may be subsequently identified as the pressure of the lowpass component at the feature time instants for each of the plurality of tactile waveforms.

Additionally, a feature pulse amplitude (e.g., of the bandpass component) of each of the plurality of tactile waveforms (e.g., each of the sensors in the tactile sensor array) at the basis time, the positive envelopes of each of the plurality of tactile waveforms (e.g., a function describing the upper bounds of the arterial pulses) at the basis time instant, and the negative envelopes of each of the plurality of transformed waveforms (e.g., a function describing the lower bounds of the arterial pulses) at the basis time instant may also be extracted as features.

Step 316 may be followed by step 318, which includes estimating blood pressure (e.g., systolic blood pressure and diastolic blood pressure) with a machine learning algorithm. For example, one possible implementation is a machine learning algorithm that utilizes regularized linear regression on the features. In general, the extracted features may be utilized for regression modeling in a machine learning algorithm to estimate blood pressure. However, in order to prevent overfitting of data derived from the features, model regularization may be desired. Regularization reduces the model complexity and the number of variables determined by the features that are extracted. In other words, regularization allows for the determination of which of the features are statistically meaningful for the regression modeling with the machine learning algorithm. For example, if five feature time instants are identified as described above and there are thirty sensors in the tactile sensor array, then there are at least two hundred and forty variables derived from the features. In order to reduce the computational burden and complexity it may be desired to utilize the regularized regression model to minimize as many variables as possible while still staying within a threshold amount of error. In some embodiments a linear regression model known as Lasso is utilized that performs variable selection and regularization of the features. Regularization decreases the coefficient magnitudes of the remaining model variables (e.g., the features that are extracted). Both variable selection and regularization are achieved via an L1-penalty to the least squares regression cost function and increase the prediction accuracy of the model. Separate Lasso regression models for mean arterial pressure, systolic blood pressure, and diastolic blood pressure may be obtained using the features extracted from the training data (e.g., the plurality of tactile waveforms from the tactile sensor array values in combination with available reference data).

While each of the steps of method 300 are discussed in a particular order, it is appreciated that steps may be omitted, added, or arranged as needed in order to estimate blood pressure with a tactile sensor array. Additionally, as illustrated in FIG. 3B, steps in method 300 may be performed in parallel.

FIGS. 4-14 illustrate examples of the various steps included in method 300 of FIG. 3, in accordance with embodiments of the present disclosure.

Figure 4:
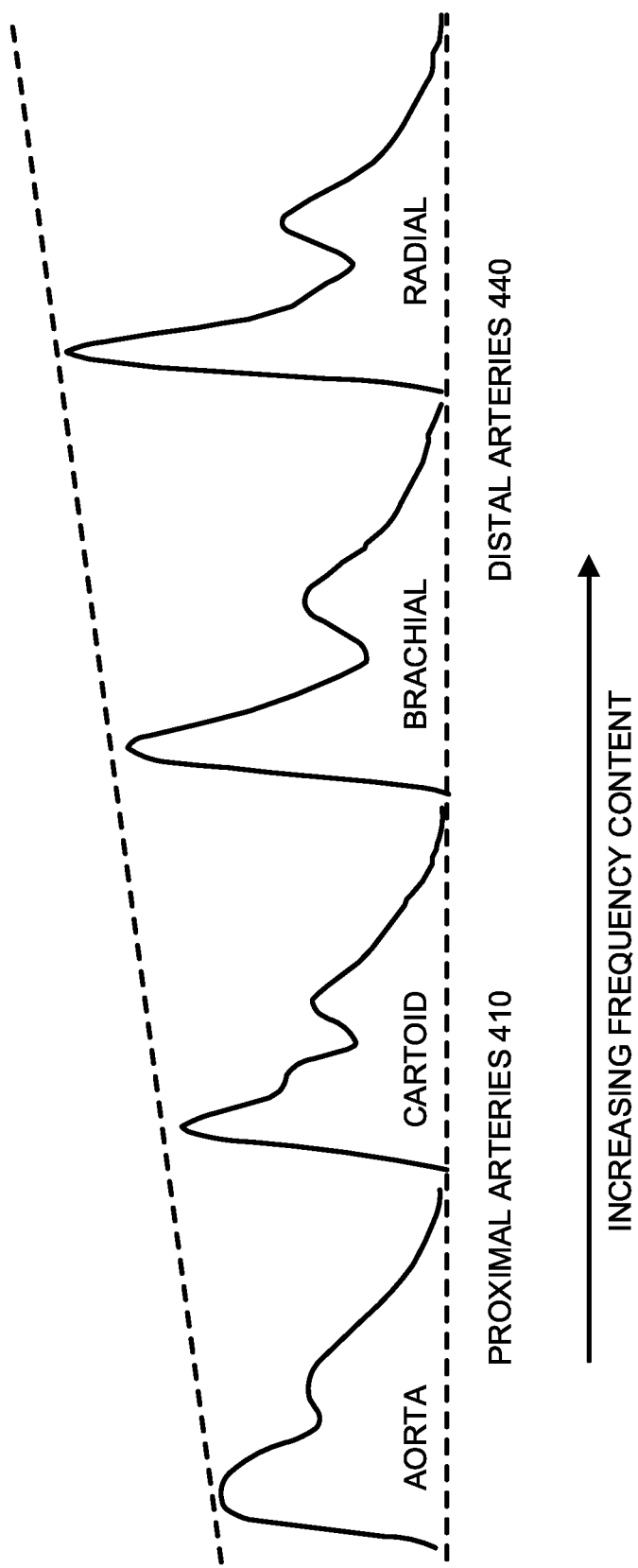
FIG. 4 illustrates representative changes in a shape of arterial pulses measured at different arteries within the circulatory system, in accordance with embodiments of the present disclosure.

FIG. 4 illustrates representative changes in a shape of arterial pulses measured at different arteries within the circulatory system, in accordance with embodiments of the present disclosure. The different shapes of the arterial pulses correspond to different waveform types. As illustrated, the frequency content increases as blood moves through the arterial tree from the proximal end (aorta) to the distal end (radial and digital arteries). Thus, in order to estimate blood pressure at proximal arteries it may be desirable to apply a transfer function to convert the plurality of tactile waveforms from a first waveform type (e.g., the digital artery) to a second waveform type (e.g., the brachial artery).

Figure 5:
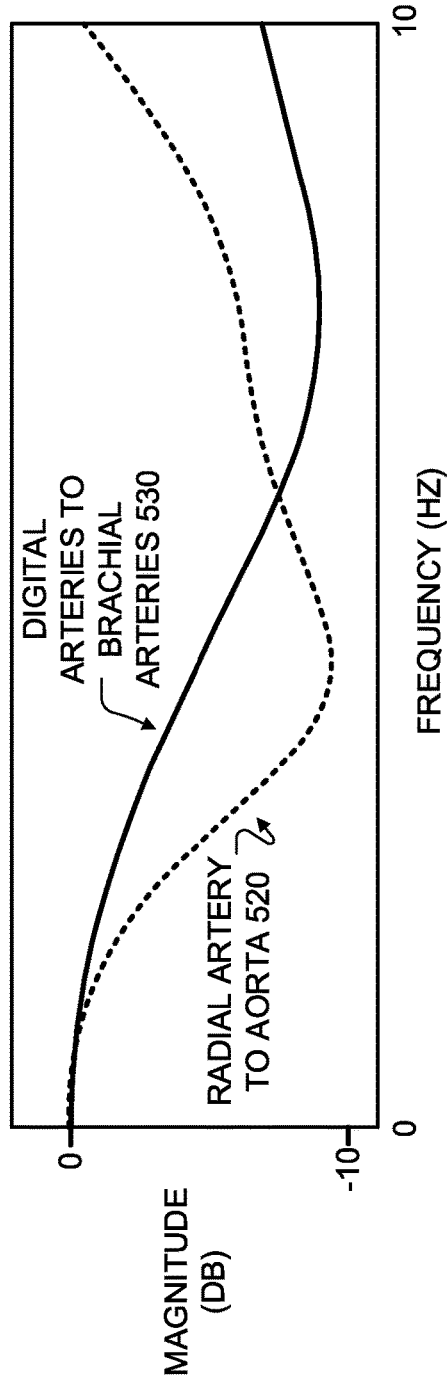
FIG. 5 illustrates plots of magnitude and phase versus frequency of different transfer functions that are applied to a plurality of tactile waveforms, in accordance with embodiments of the present disclosure.
Figure 5:
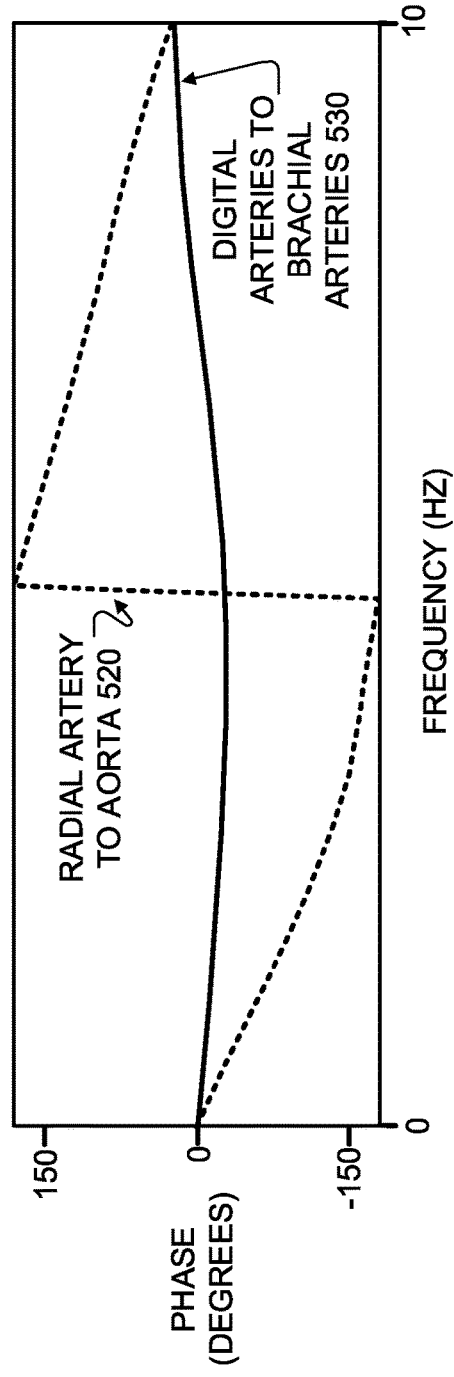

FIG. 5 illustrates plots of magnitude and phase versus frequency of different transfer functions that are applied to the plurality of tactile waveforms, in accordance with embodiments of the present disclosure. As illustrated, the different transfer functions include converting pressure measurements from digital arteries to brachial arteries 530 and converting the radial artery to aorta 520.

Figure 6:
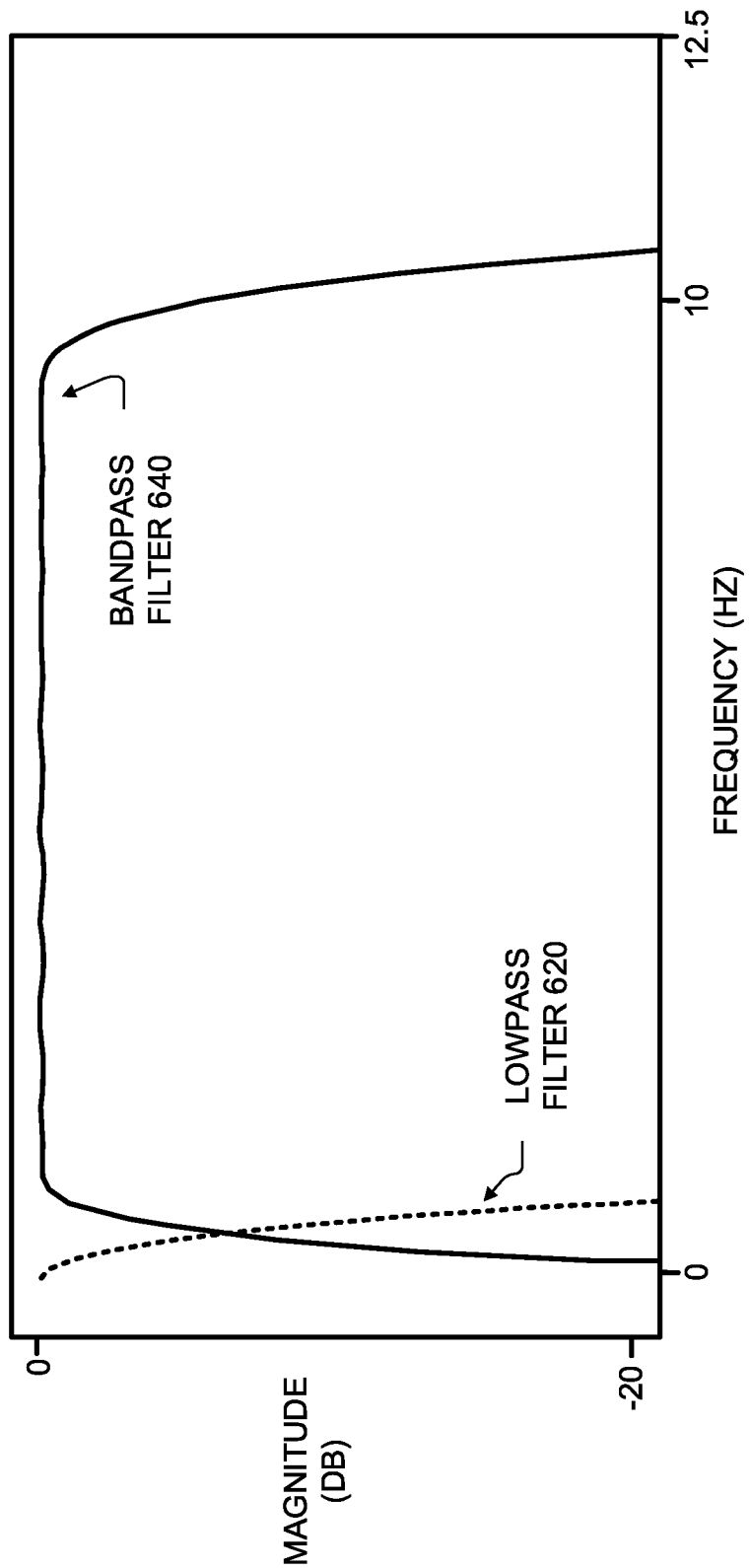
FIG. 6 illustrates the frequency responses of a lowpass filter and a bandpass filter that are applied to the plurality of tactile waveforms, in accordance with an embodiment of the present disclosure.

FIG. 6 illustrates the frequency responses of a lowpass filter 620 and a bandpass filter 640 that are applied to the plurality of tactile waveforms, in accordance with an embodiment of the present disclosure. As illustrated, lowpass filter 620 selects a portion of the plurality of tactile waveforms having a frequency lower than a predetermined cut-off frequency, while bandpass filter 640 selects a portion of the plurality of tactile waveforms within a certain frequency range. Thus, the lowpass component is representative of the pressure applied over the first time period without the pressure fluctuations, while the bandpass component is representative of the pressure fluctuations over the first time period.

Figure 7:
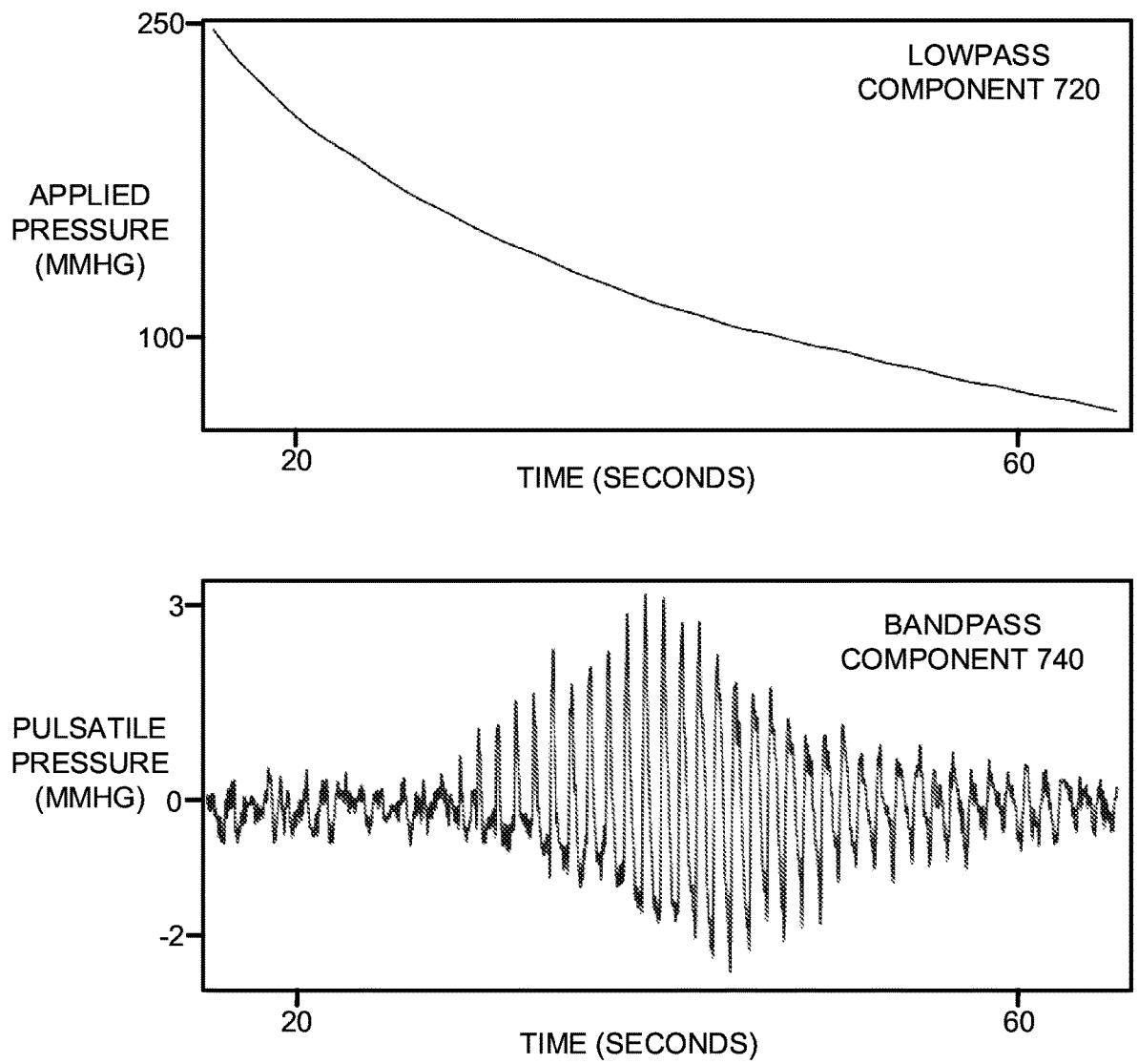
FIG. 7 illustrates the lowpass component and the bandpass component of the tactile waveform as pressure with respect to time after applying one or more filters, in accordance with an embodiment of the present disclosure.

FIG. 7 illustrates lowpass component 720 and bandpass component 740 of the tactile waveform as pressure with respect to time after applying one or more filters (e.g., lowpass filter 620 and bandpass filter 640 of FIG. 6), in accordance with an embodiment of the present disclosure. As illustrated, low pass component 720 correspond to the pressure applied to the tactile sensor array by the digital artery of the finger. Bandpass component 740 corresponds to the pressure fluctuations (e.g., arterial pulses) caused by blood flow within the digital artery of the finger.

Figure 8:
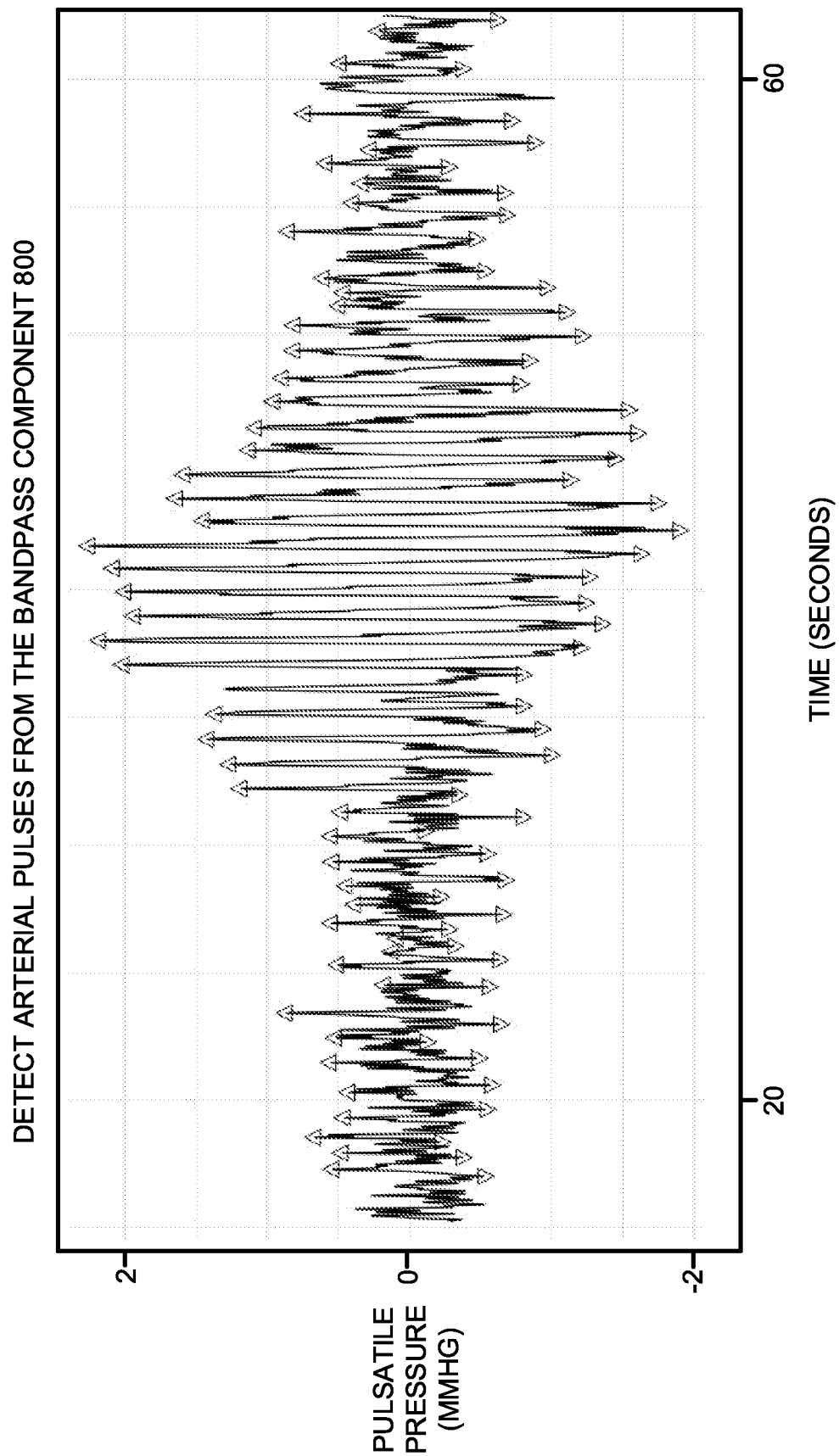
FIG. 8 illustrates detecting arterial pulses from the bandpass component of the tactile waveform, in accordance with an embodiment of the present disclosure.

FIG. 8 illustrates detecting arterial pulses from the bandpass component of one of the tactile waveforms included in the plurality of tactile waveforms, in accordance with an embodiment of the present disclosure. Each of the arterial pulses has a corresponding amplitude, one of which has a maximum amplitude. The pulsatile pressure shows the periodic change in pressure over the first time period due, at least in part, to blood flow within the digital artery. Thus, by determining the duration between peaks and valleys of each periodic event in the bandpass region, the pulse or heart rate of the user can be estimated. Similarly, as discussed previously, features may be extracted after identifying each of the arterial pulses.

Figure 9:
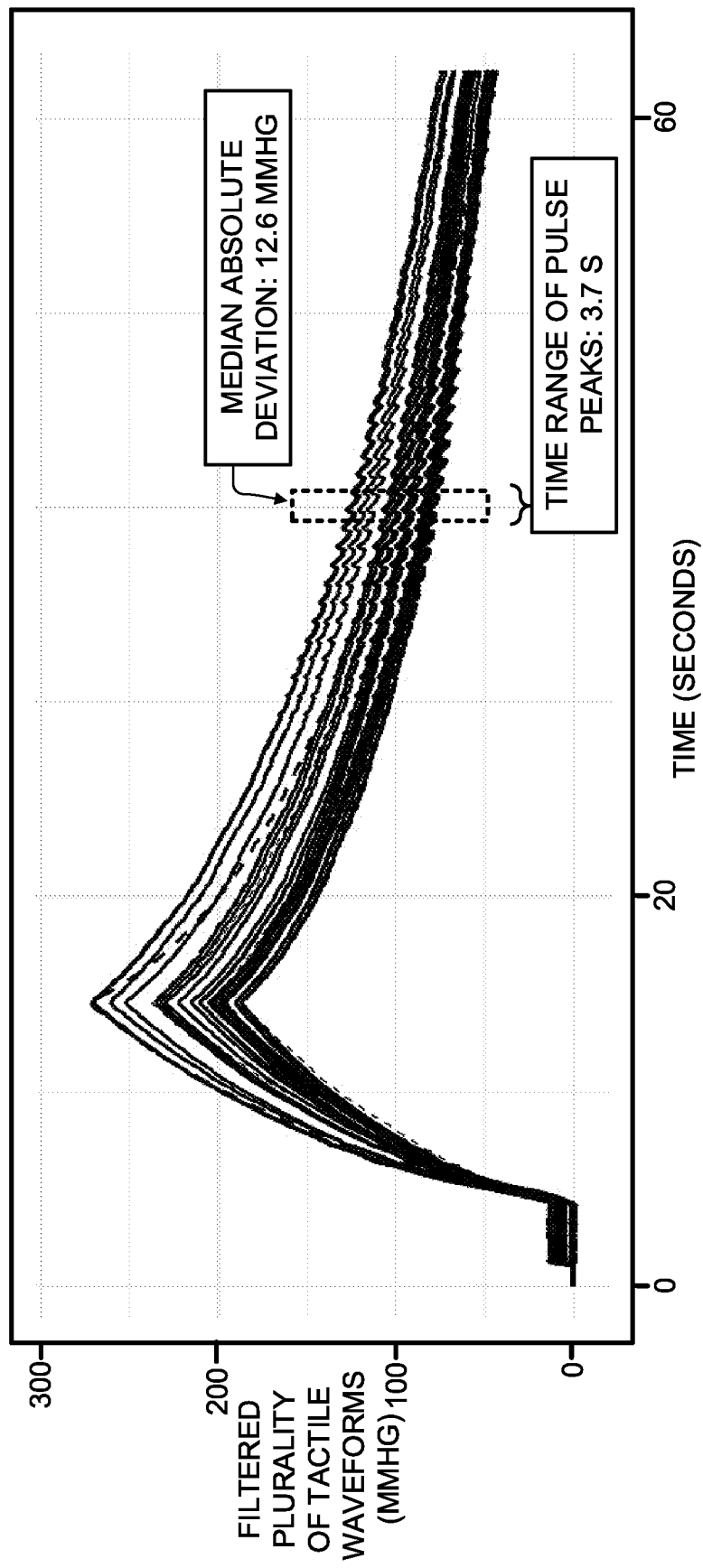
FIG. 9 illustrates determining whether to accept or reject the tactile waveform as valid, in accordance with an embodiment of the present disclosure.

FIG. 9 illustrates determining whether to accept or reject the tactile waveform as valid, in accordance with an embodiment of the present disclosure. As illustrated, comparison metrics of the plurality of tactile waveforms are compared to a pressure spread threshold and/or a temporal spread threshold. The median absolute deviation (e.g., pressure spread) is 12.6 mmHg, which may be less than the pressure spread threshold value. Similarly, the time range of the corresponding maximum pulse amplitudes of maximum arterial pulse elements is 3.7 seconds, which may be less than a temporal time spread threshold.

Figure 10:
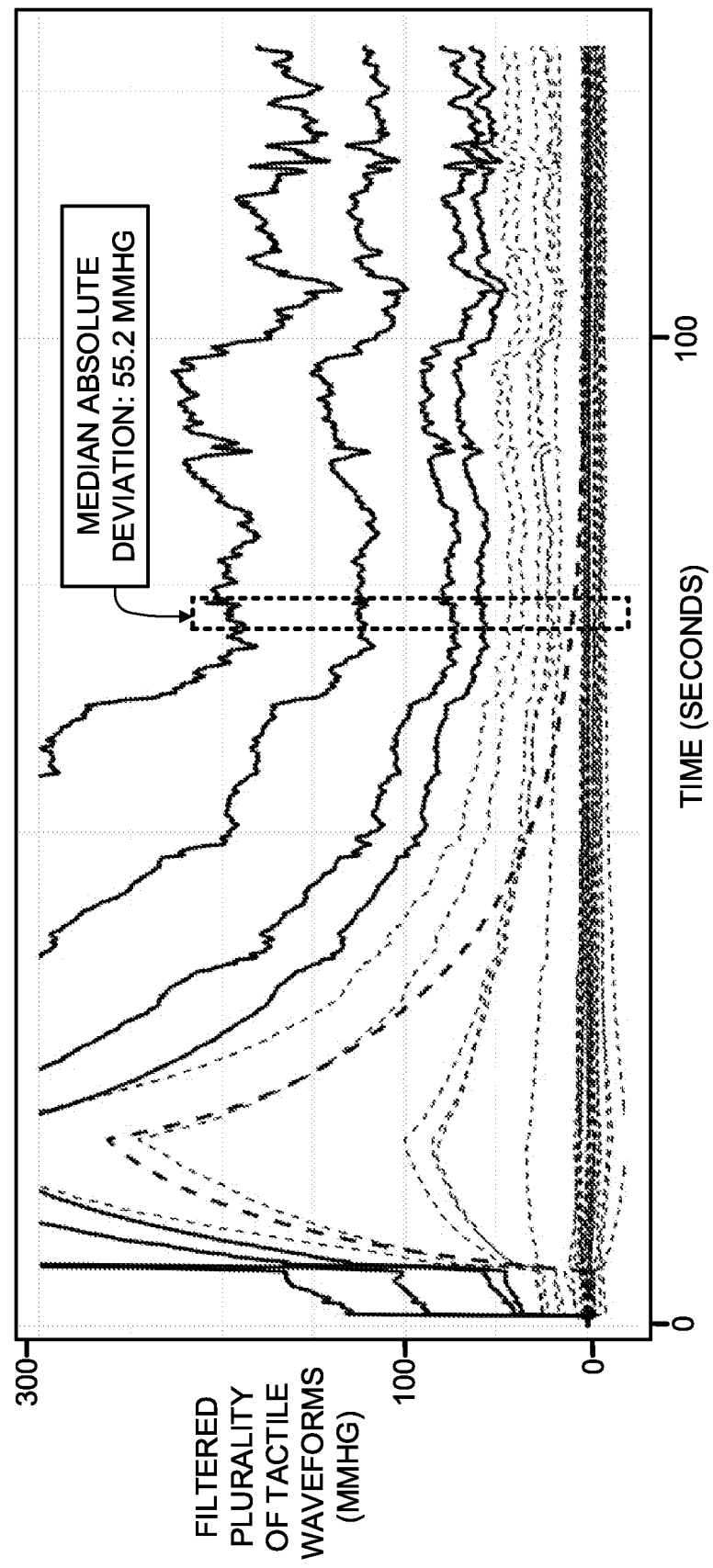
FIG. 10 illustrates determining whether to accept or reject the tactile waveform as valid, in accordance with an embodiment of the present disclosure.

FIG. 10 illustrates determining whether to accept or reject the tactile waveform as valid, in accordance with an embodiment of the present disclosure. As illustrated, the median absolute deviation (e.g., pressure spread) is 55.2 mmHg, which may be greater than the pressure spread threshold value and thus result in the determination that the measurement consisting of a plurality of tactile waveforms is not valid.

Figure 11:
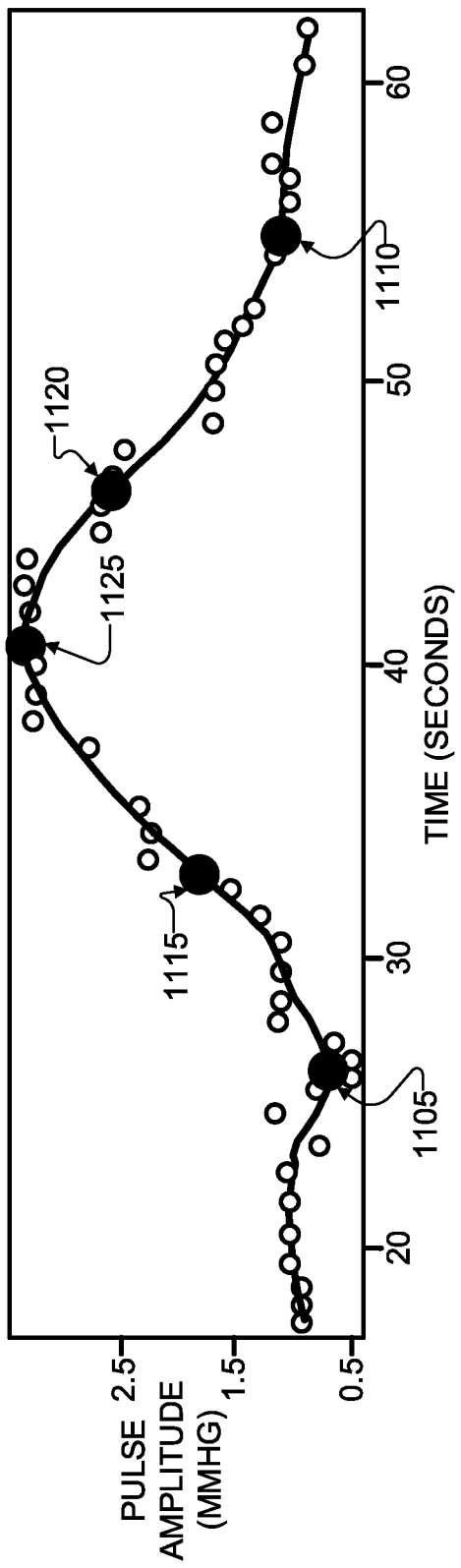
FIG. 11 illustrates extracting features from the tactile waveform, in accordance with an embodiment of the present disclosure.

FIG. 11 illustrates extracting features from the tactile waveform, in accordance with an embodiment of the present disclosure. As illustrated, each open circle represents a raw pulse amplitude of an arterial pulse included in the arterial pulses of the first tactile waveform (e.g., the tactile waveform including the basis arterial pulse having a pulse amplitude greater than any other one of the arterial pulses included in all of the plurality of tactile waveforms). It is possible to determine the feature time instants based on the feature curve of the pulse amplitudes during the first time period. The features include a left foot 1105 of the feature curve, a right foot 1110 of the feature curve, a maximum slope of the feature curve 1115, a minimum slope of the feature curve 1120, and a maximum pulse amplitude 1125. The feature curve may also be finely tuned based on hyperparameter values that may be manually or automatically determined. The hyperparameters may include a span of the curve smoothed with a Loess regression fit and a slope threshold for determining the foot of the curve (e.g., left foot 1105 and right foot 1110). Regression modeling with a machine learning algorithm may be used to generate a fit of the features. The model may further be fine-tuned with the hyperparameter values.

Figure 12:
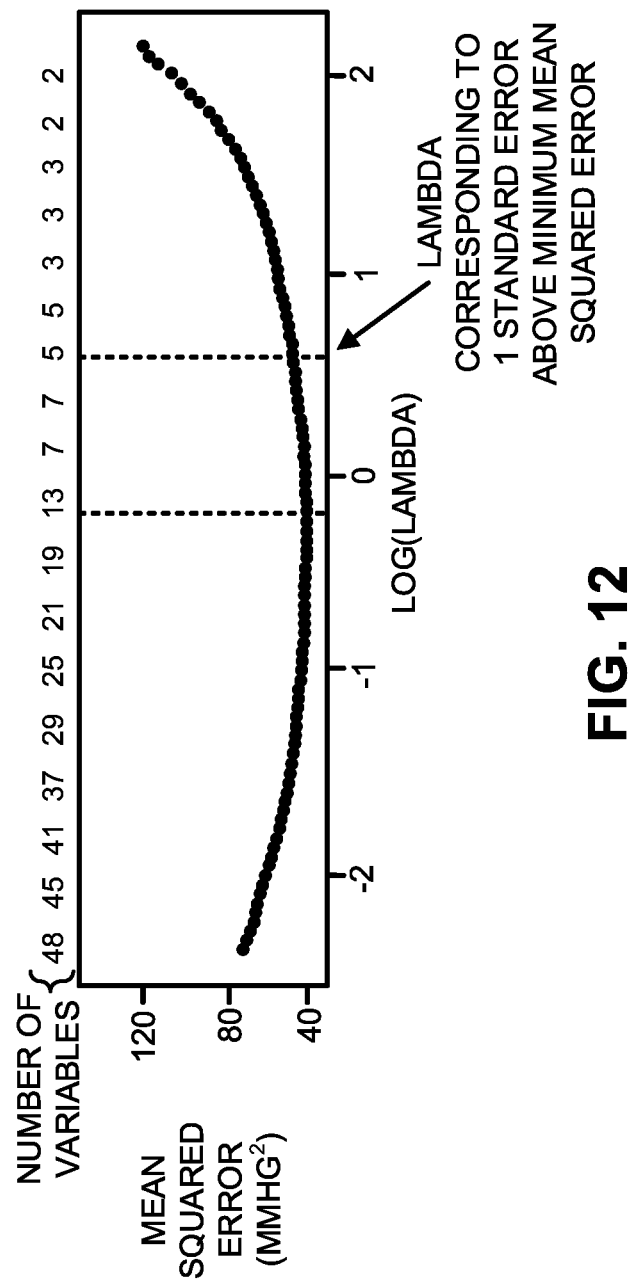
FIG. 12 illustrates error of a machine learning algorithm that utilizes regularized linear regression on the features to estimate blood pressure, in accordance with an embodiment of the present disclosure.

FIG. 12 illustrates error of a machine learning algorithm that utilizes regularized linear regression on the features to estimate blood pressure, in accordance with an embodiment of the present disclosure. The regression model may reduce the number of relevant features that were extracted and subsequently reduce the complexity of the system. As illustrated, a Lasso model is utilized which significantly reduces the number of variables (e.g., features) from two hundred and forty to a selected value of five. The regression model may utilize cross validation within the training data (e.g., the plurality of tactile waveforms from the tactile sensor array in combination with reference data). Such validation can be utilized to determine mean squared error of blood pressure estimation. It may be desirable to select the largest value of the regularization parameter lambda such that the cross validation error is within one standard error of the minimum mean squared error.

Figure 13A:
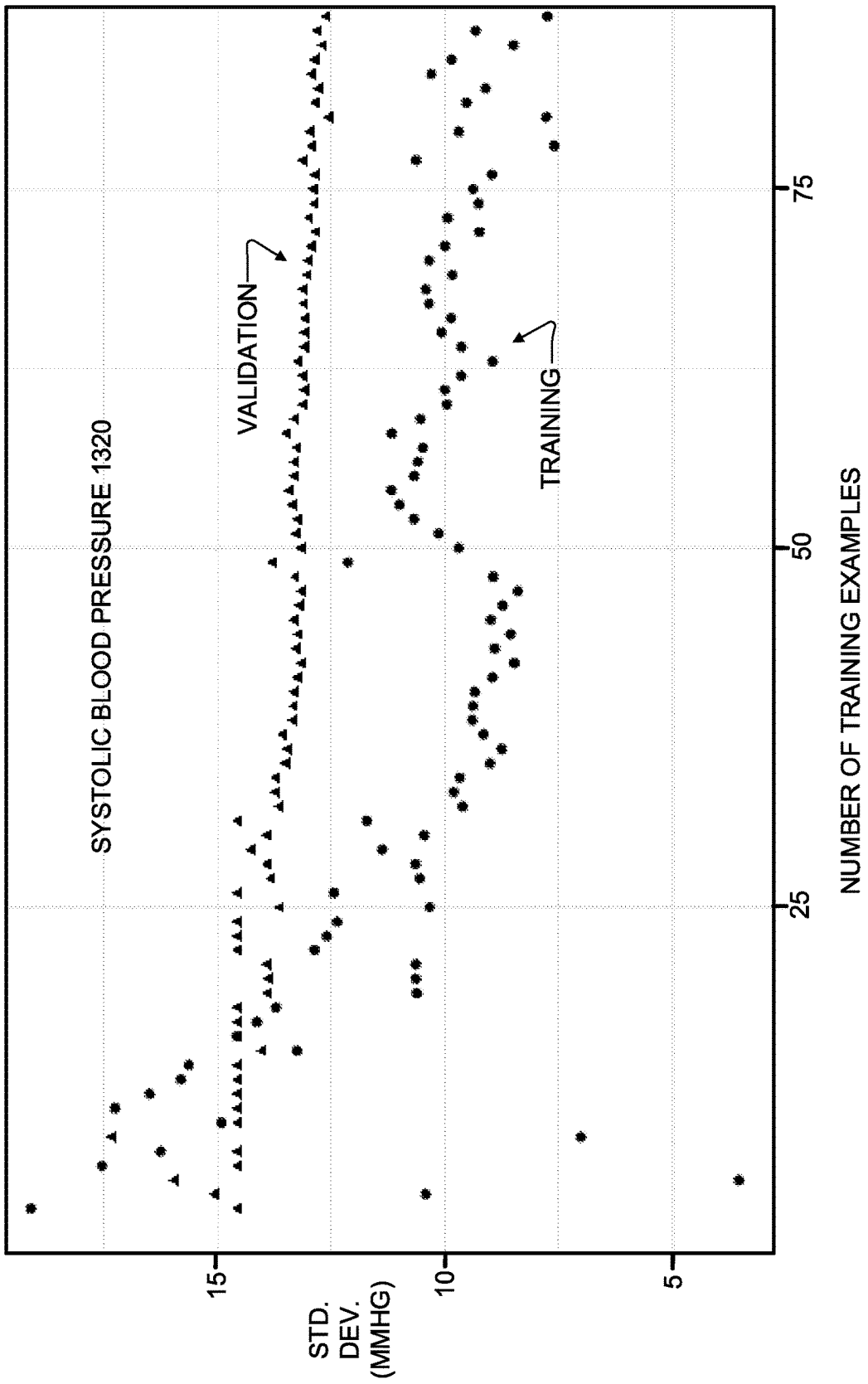
FIGS. 13A and 13B illustrates learning curves of the machine learning algorithm to validate estimated blood pressure with reference data, in accordance with an embodiment of the present disclosure.
Figure 13B:
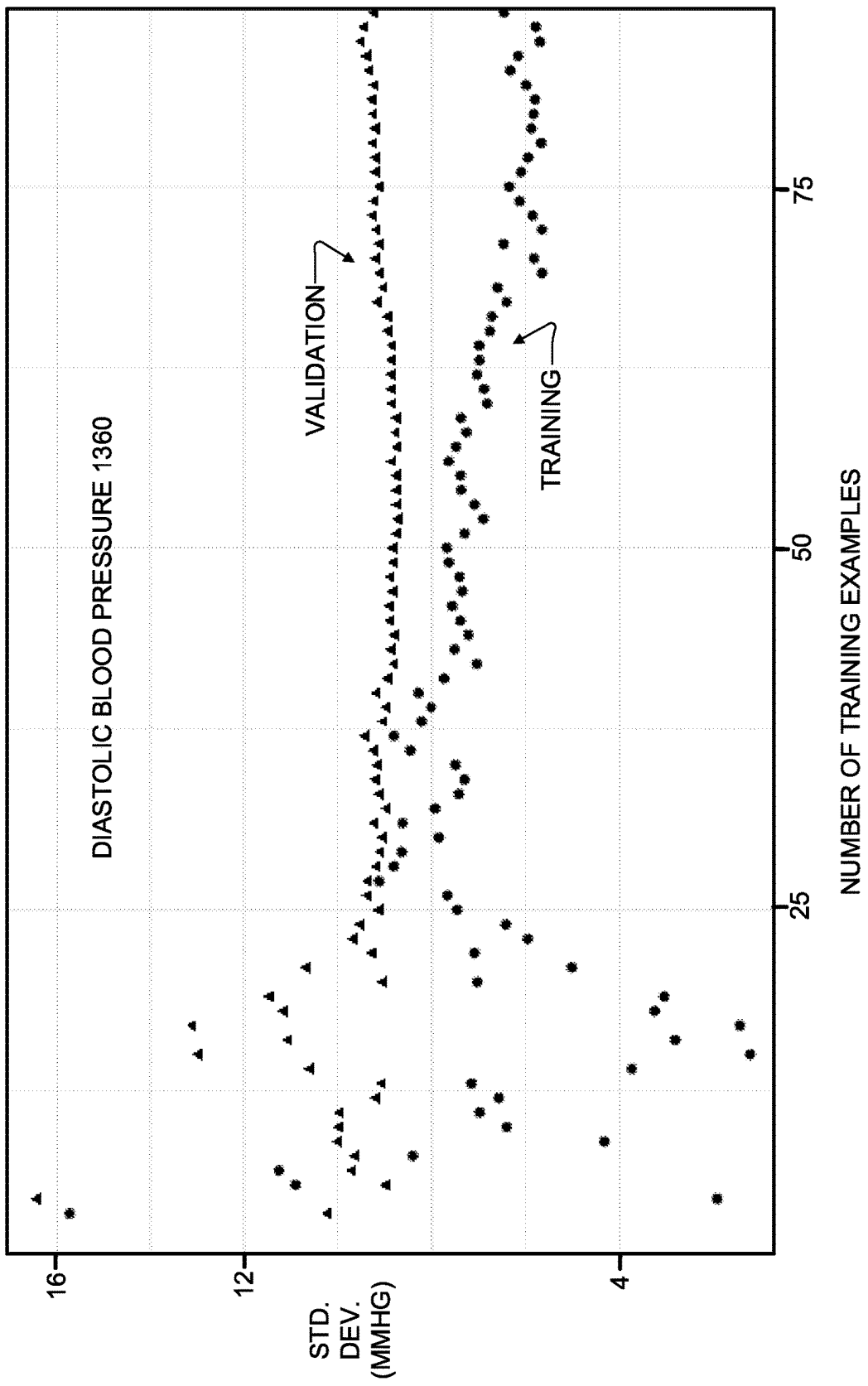

FIGS. 13A and 13B illustrates learning curves of the machine learning algorithm to validate estimated blood pressure with reference data, in accordance with an embodiment of the present disclosure. The learning curves compare the standard deviation of the estimated blood pressure (e.g., systolic blood pressure 1320 of FIG. 13A and diastolic blood pressure 1360 of FIG. 13B) determined with regression modeling to reference data based on the number of training examples.

Figure 14:
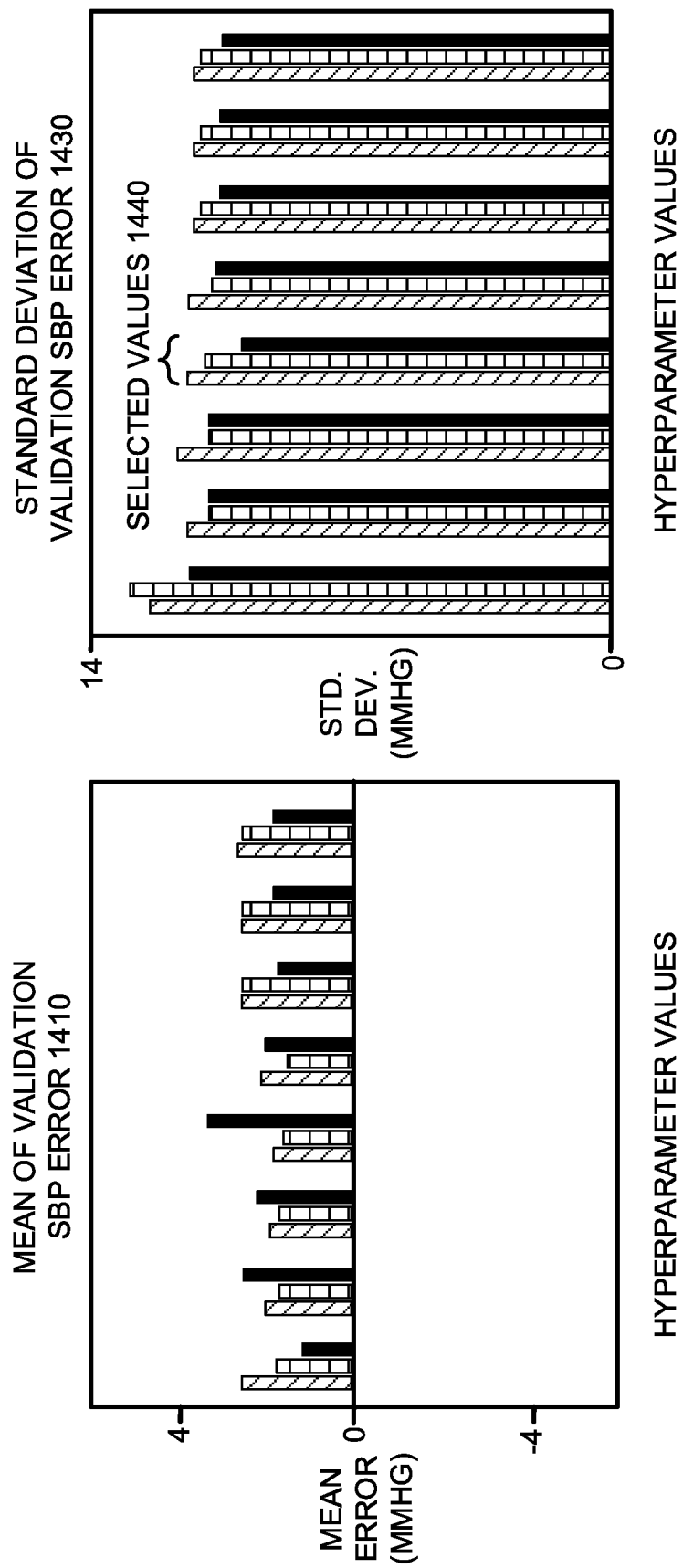
FIG. 14 illustrates a comparison of error for blood pressure estimation using different hyperparameter values with different transfer functions, in accordance with an embodiment of the present disclosure.

FIG. 14 illustrates a comparison of error for blood pressure estimation using different hyperparameter values with different transfer functions, in accordance with an embodiment of the present disclosure. For example, selected values 1440 are based on hyperparameter values of Loess 0.25 and foot 0.20.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A finger-wearable blood pressure monitoring device, the device comprising:
   a cuff,
   a tactile sensor array disposed on or adjacent to an inward facing surface of the cuff, wherein the tactile sensor array includes a plurality of sensors; and
   control circuitry coupled to the tactile sensor array, the control circuitry including logic that when executed by the control circuitry causes the finger-wearable blood pressure monitoring device to perform operations including:
      monitoring, over a first time period, a pressure applied to each of the plurality of sensors;
      generating a plurality of tactile waveforms in response to monitoring the pressure, wherein each of the plurality of tactile waveforms is representative of the pressure applied to a respective one of the plurality of sensors over the first time period;
      decomposing each of the plurality of tactile waveforms into a lowpass component and a bandpass component via one or more filters, wherein the bandpass component corresponds to pressure fluctuations over the first time period due, at least in part, to blood flow within a digital artery, and wherein the lowpass component is representative of a baseline pressure corresponding to the pressure applied with at least some of the pressure fluctuations filtered out;
      extracting features from at least one of the lowpass component or the bandpass component of each of the plurality of tactile waveforms; and
      estimating, blood pressure using a machine learning model to generate a fit of the features extracted from the at least one of the lowpass component or the bandpass component of each of the plurality of tactile waveforms.

2. The device of claim 1, wherein the control circuitry includes further logic that when executed causes the finger-wearable blood pressure monitoring device to perform further operations including:
   applying a transfer function to each of the plurality of tactile waveforms to convert each of the plurality of tactile waveforms from a first waveform type to a second waveform type, wherein the first waveform type and the second waveform type represent blood pressure monitored at different arteries.

3. The device of claim 1, wherein the control circuitry includes further logic that when executed causes the finger-wearable blood pressure monitoring device to perform further operations including:
   detecting arterial pulses from the bandpass component for each of the plurality tactile waveforms, wherein each of the arterial pulses are based, at least in part, on the pressure fluctuations due to the blood flow.

4. The device of claim 3, wherein the control circuitry includes further logic that when executed causes the finger-wearable blood pressure monitoring device to perform further operations including:

determining at least one comparison metric based on at least one of the plurality of tactile waveforms; and
determining whether to accept or reject at least one of the plurality of tactile waveforms generated by the tactile sensor array by comparing the comparison metric to a corresponding threshold value.

5. The device of claim 4, wherein the control circuitry includes further logic that when executed causes the finger-wearable blood pressure monitoring device to perform further operations including:
identifying a maximum amplitude arterial pulse for each of the plurality of tactile waveforms, wherein the maximum amplitude arterial pulse is one of the arterial pulses having a pulse amplitude greater than any other one of the arterial pulses in a corresponding one of the plurality of tactile waveforms.

6. The device of claim 5, wherein the comparison metric includes at least the maximum amplitude arterial pulse, and wherein the corresponding threshold value is a pulse amplitude threshold.

7. The device of claim 6, wherein the control circuitry includes further logic that when executed causes the finger-wearable blood pressure monitoring device to perform further operations including:
identifying a first set of tactile waveforms included in the plurality of tactile waveforms based on comparing the maximum amplitude arterial pulse to the pulse amplitude threshold; and
determining a temporal spread metric based on time instants of the maximum amplitude arterial pulse of the first set of tactile waveforms, wherein the temporal spread metric is included in the at least one comparison metric, and wherein the corresponding threshold value is a temporal spread threshold; and
comparing the temporal spread metric of the first set of tactile waveforms to the temporal spread threshold.

8. The device of claim 5, wherein the control circuitry includes further logic that when executed causes the finger-wearable blood pressure monitoring device to perform further operations including:
comparing the maximum arterial pulse of each of the plurality of tactile waveforms to one another to determine a basis arterial pulse, wherein the pulse amplitude of the basis arterial pulse is greater than the pulse amplitude of any other one of the arterial pulses included in the plurality of tactile waveforms, wherein the basis arterial pulse is at a basis time instant within the first time period.

9. The device of claim 8, wherein the control circuitry includes further logic that when executed causes the finger-wearable blood pressure monitoring device to perform further operations including:
determining a pressure spread metric based on the lowpass component at the basis time instant for each of the plurality of tactile waveforms, wherein the at least one comparison metric includes the pressure spread metric, and wherein the corresponding threshold value is a pressure spread threshold; and
comparing the pressure spread metric of the plurality of tactile waveforms to the pressure spread threshold.

10. The device of claim 1, wherein the control circuitry includes further logic that when executed causes the finger-wearable blood pressure monitoring device to perform further operations including:
detecting arterial pulses from the bandpass component for each of the plurality of tactile waveforms, wherein each of the arterial pulses are based, at least in part, on the pressure fluctuations due to the blood flow;
identifying a maximum amplitude arterial pulse for each of the plurality of tactile waveforms, wherein the maximum amplitude arterial pulse is one of the arterial pulses having a pulse amplitude greater than any other one of the arterial pulses in a corresponding one of the plurality of tactile waveforms; and
comparing the maximum arterial pulse of each of the plurality of tactile waveforms to one another to determine a basis arterial pulse, wherein the pulse amplitude of the basis arterial pulse is greater than the pulse amplitude of any other one of the arterial pulses included in the plurality of tactile waveforms, wherein the basis arterial pulse is at a basis time instant within the first time period.

11. The device of claim 10, wherein the control circuitry includes further logic that when executed causes the finger-wearable blood pressure monitoring device to perform further operations including:
computing a feature curve, corresponding to the fit provided by the machine learning model, representing the pulse amplitude of the arterial pulses included in a first tactile waveform over the first time period, where the arterial pulses of the first tactile waveform includes the basis arterial pulse; and
determining feature time instants based on at least one of a maximum pulse amplitude of the feature curve, a maximum slope of the feature curve, a minimum slope of the feature curve, or a foot of the feature curve, and wherein the features include a pressure of the lowpass component at the feature time instants for each of the plurality of tactile waveforms.

12. The device of claim 10, wherein the control circuitry includes further logic that when executed causes the finger-wearable blood pressure monitoring device to perform further operations including:
computing at least one of a feature pulse amplitude, a positive envelope, or a negative envelope for each of the plurality of tactile waveforms at the basis time instant, wherein the features include at least one of the pulse amplitude, the positive envelope component, or the negative envelope.

13. The device of claim 1, wherein the control circuitry includes further logic that when executed causes the finger-wearable blood pressure monitoring device to perform further operations including:
calculating systolic blood pressure and diastolic blood pressure estimates using the machine learning model trained to provide regularized linear regression on the features.

14. The device of claim 1, wherein each of the plurality of sensors included in the tactile sensor array are capacitive sensors, and wherein the plurality of tactile waveforms are based, at least in part, on capacitance values of the capacitive sensors.

15. A method for estimating blood pressure, the method including:
monitoring, over a first time period, a pressure applied to a plurality of sensors included in a tactile sensor array;
generating a plurality of tactile waveforms in response to monitoring the pressure, wherein each of the plurality of tactile waveforms corresponds to the pressure applied to a respective one of the plurality of sensors over the first time period;
decomposing each of the plurality of tactile waveforms into a lowpass component and a bandpass component via one or more filters, wherein the bandpass component corresponds to pressure fluctuations over the first time period due, at least in part, to blood flow within a digital artery, and wherein the lowpass component is representative of a baseline pressure corresponding to the pressure applied with at least some of the pressure fluctuations filtered out;

extracting features from at least one of the lowpass component and the bandpass component of each of the plurality of tactile waveforms; and estimating, blood pressure using a machine learning model to generate a fit of the features extracted from the at least one of the lowpass component or the bandpass component of each of the plurality of tactile waveforms.

16. The method of claim 15, further comprising:
applying a transfer function to each of the plurality of tactile waveforms to convert each of the plurality of tactile waveforms from a first waveform type to a second waveform type, wherein the first waveform type and the second waveform type represent blood pressure monitored at different arteries.

17. The method of claim 15, further comprising:
detecting arterial pulses from the bandpass component for each of the plurality tactile waveforms, wherein each of the arterial pulses are based, at least in part, on the pressure fluctuations due to the blood flow.

18. The method of claim 17, further comprising:
determining at least one comparison metric based on at least one of the plurality of tactile waveforms; and
determining whether to accept or reject at least one of the plurality of tactile waveforms generated by the tactile sensor array by comparing the comparison metric to a corresponding threshold value.

19. The method of claim 18, further comprising:
identifying a maximum amplitude arterial pulse for each of the plurality of tactile waveforms, wherein the maximum amplitude arterial pulse is one of the arterial pulses having a pulse amplitude greater than any other one of the arterial pulses in a corresponding one of the plurality of tactile waveforms.

20. The method of claim 19, wherein the comparison metric includes at least the maximum amplitude arterial pulse, and wherein the corresponding threshold value is a pulse amplitude threshold.

21. The method of claim 20, further comprising:
identifying a first set of tactile waveforms included in the plurality of tactile waveforms based on comparing the maximum amplitude arterial pulse to the pulse amplitude threshold; and
determining a temporal spread metric based on time instants of the maximum amplitude arterial pulse of the first set of tactile waveforms, wherein the temporal spread metric is included in the at least one comparison metric, and wherein the corresponding threshold value is a temporal spread threshold; and
comparing the temporal spread metric of the first set of tactile waveforms to the temporal spread threshold.

22. The method of claim 19, further comprising:
comparing the maximum arterial pulse of each of the plurality of tactile waveforms to one another to determine a basis arterial pulse, wherein the pulse amplitude of the basis arterial pulse is greater than the pulse amplitude of any other one of the arterial pulses included in the plurality of tactile waveforms, wherein the basis arterial pulse is at a basis time instant within the first time period.

23. The device of claim 22, further comprising:
determining a pressure spread metric based on the lowpass component at the basis time instant for each of the plurality of tactile waveforms, wherein the at least one comparison metric includes the pressure spread metric, and wherein the corresponding threshold value is a pressure spread threshold; and
comparing the pressure spread metric of the plurality of tactile waveforms to the pressure spread threshold.

24. The method of claim 15, further comprising:
detecting arterial pulses from the bandpass component for each of the plurality of tactile waveforms, wherein each of the arterial pulses are based, at least in part, on the pressure fluctuations due to the blood flow;
identifying a maximum amplitude arterial pulse for each of the plurality of tactile waveforms, wherein the maximum amplitude arterial pulse is one of the arterial pulses having a pulse amplitude greater than any other one of the arterial pulses in a corresponding one of the plurality of tactile waveforms; and
comparing the maximum arterial pulse of each of the plurality of tactile waveforms to one another to determine a basis arterial pulse, wherein the pulse amplitude of the basis arterial pulse is greater than the pulse amplitude of any other one of the arterial pulses included in the plurality of tactile waveforms, wherein the basis arterial pulse is at a basis time instant within the first time period.

25. The method of claim 24, further comprising:
computing a feature curve, corresponding to the fit provided by the machine learning model, representing the pulse amplitude of the arterial pulses included in a first tactile waveform over the first time period, where the arterial pulses of the first tactile waveform includes the basis arterial pulse; and
determining feature time instants based on at least one of a maximum pulse amplitude of the feature curve, a maximum slope of the feature curve, a minimum slope of the feature curve, or a foot of the feature curve, and wherein the features include a pressure of the lowpass component at the feature time instants for each of the plurality of tactile waveforms.

26. The method of claim 24, further comprising:
computing at least one of a feature pulse amplitude, a positive envelope, or a negative envelope for each of the plurality of tactile waveforms at the basis time instant, wherein the features include at least one of the pulse amplitude, the positive envelope component, or the negative envelope.

27. The method of claim 15, further comprising:
calculating systolic blood pressure and diastolic blood pressure estimates using the machine learning model trained to provide regularized linear regression on the features.

* * * * *